(12) United States Patent
Bergmann

(10) Patent No.: US 11,726,101 B2
(45) Date of Patent: *Aug. 15, 2023

(54) ADRENOMEDULLIN ASSAYS AND METHODS FOR DETERMINING MATURE ADRENOMEDULLIN

(71) Applicant: SPHINGOTEC GMBH, Hennigsdorf (DE)

(72) Inventor: Andreas Bergmann, Berlin (DE)

(73) Assignee: SPHINGOTEC GMBH, Hennigsdorf (DE)

(*) Notice: Subject to any disclaimer, the term of this patent is extended or adjusted under 35 U.S.C. 154(b) by 37 days.

This patent is subject to a terminal disclaimer.

(21) Appl. No.: 17/349,134

(22) Filed: Jun. 16, 2021

(65) Prior Publication Data
US 2021/0311078 A1    Oct. 7, 2021

Related U.S. Application Data

(60) Continuation of application No. 15/344,784, filed on Nov. 7, 2016, now Pat. No. 11,067,586, which is a division of application No. 14/358,147, filed as application No. PCT/EP2012/072928 on Nov. 16, 2012, now Pat. No. 9,535,060.

(30) Foreign Application Priority Data

| Nov. 16, 2011 | (EP) | 11189447 |
| Nov. 16, 2011 | (EP) | 11189448 |
| Nov. 16, 2011 | (EP) | 11189449 |
| Nov. 16, 2011 | (EP) | 11189450 |
| Nov. 16, 2011 | (EP) | 11189452 |
| Mar. 16, 2012 | (EP) | 12160014 |
| Mar. 16, 2012 | (EP) | 12160015 |
| Mar. 16, 2012 | (EP) | 12160016 |
| Mar. 16, 2012 | (EP) | 12160017 |
| Mar. 16, 2012 | (EP) | 12160018 |
| Sep. 27, 2012 | (EP) | 12186449 |

(51) Int. Cl.
*G01N 33/53* (2006.01)
*G01N 33/74* (2006.01)

(52) U.S. Cl.
CPC ........ *G01N 33/74* (2013.01); *G01N 2800/26* (2013.01); *G01N 2800/52* (2013.01)

(58) Field of Classification Search
None
See application file for complete search history.

(56) References Cited

U.S. PATENT DOCUMENTS

| 5,639,855 A | 6/1997 | Kitamura |
| 2007/0212742 A1 | 9/2007 | Bergmann et al. |
| 2011/0217301 A1* | 9/2011 | Freishtat ............ A61K 31/343 |
| | | 435/375 |
| 2013/0224187 A1* | 8/2013 | Rother ............... A61K 47/60 |
| | | 536/23.53 |

FOREIGN PATENT DOCUMENTS

WO    2004/090546 A1    10/2004

OTHER PUBLICATIONS

International Search Report dated Feb. 20, 2013 issued in corresponding PCT/EP2012/072928 application (pp. 1-5).
K. Kitamura et al. "The Intermediate Form of Glycine-Extended Adrenomedullin Is the Major Circulating Molecular Form in Human Plasma", Biochemical and Biophysical Research Communications, vol. 244, No. 2 (Mar. 1, 1998) pp. 551-555.
L.K. Lewis et al., "Adrenomedullin (1-52) Measured in Human Plasma by Radioimmunoassay: Plasma Concentration, Adsorption, and Storage", Clinical Chemistry, vol. 44, No. 3 (Mar. 1, 1998) pp. 571-577.
Ohta et al., "One-Step Direct Assay for Mature-type Adrenomedullin with Monoclonal Antibodies", Clinical Chemistry, vol. 45, No. 2, 1999, pp. 244 251.
Van Der Vekiens et al., Human and equine cardiovascular endocrinology: beware to compare, Cardiovascular Endocrinology 2013, vol. 2, No. 4, pp. 67-76 (Year: 2013).
Torzewski et al., Animal Models of C-Reactive Protein, Hindawl Publishing Corporation, Mediators of Inflammation, vol. 2014, Article ID 683598, 2014, pp. 1-7. (Year: 2014).

* cited by examiner

*Primary Examiner* — Gary Counts
(74) *Attorney, Agent, or Firm* — Millen, White, Zelano & Branigan, PC; Ryan Pool

(57) ABSTRACT

An in vitro method for therapy follow-up in septic patients wherein the concentration of mature ADM 1-52 and/or mature ADM 1-52-Gly in a sample of bodily fluid of said septic patient is determined using an assay containing two binders that bind to two different regions within the region of mature adrenomedullin and/or adrenomedullin-Gly that is aminoacid 21-52-amid SEQ ID No. 1 or aminoacid 21-52-Gly SEQ ID No. 2 wherein each of said regions contains at least 4 or 5 amino acids, and further assays and calibration methods.

18 Claims, 10 Drawing Sheets

Specification includes a Sequence Listing.

Fig. 3: Predicting in-hospital mortality

Predicting in-hospital mortality

- ADM is independent from Apache and provides additional prognostic information:

| | LR $\chi^2$ | d.f. | p value |
|---|---|---|---|
| adding Apache (Apache) to hADM | 7.14 | 1 | 0.0075 |
| adding hADM (hADM) to Apache | 6.39 | 1 | 0.0115 |

- AUC(ADM plus APACHE): 0.799 (vs. 0.783 for APACHE alone)
- Chi$^2$: 26.4 (vs. 20.0 for APACHE)

ADRENOMEDULLIN ASSAYS AND METHODS FOR DETERMINING MATURE ADRENOMEDULLIN

This application is a continuation of U.S. application Ser. No. 15/344,784 filed 11 Jul. 2016 (now U.S. Pat. No. 11,067,586), which is a Division of Ser. No. 14/358,147 file 14 May 2014 (now U.S. Pat. No. 9,535,060), which is a National Stage Entry of PCT/EP2012/072928 filed Nov. 16, 2012.

Subject of the present invention is an in vitro method for therapy follow-up in septic patients wherein the concentration of mature ADM 1-52 and/or mature ADM 1-52-Gly in a sample of bodily fluid of said septic patient is determined using an assay comprising two binders that bind to two different regions within the region of mature adrenomedullin and/or adrenomedullin-Gly that is amino acid 21-52-amid SEQ ID No. 1 or amino acid 21-52-Gly SEQ ID No. 2 wherein each of said regions comprises at least 4 or 5 amino acids.

Subject of the present invention are further assays and calibration methods.

The peptide adrenomedullin (ADM) was described for the first time in Kitamura et al., (cf. 1; numerical data are based on the attached list of references) as a novel hypotensive peptide comprising 52 amino acids, which had been isolated from a human pheochromocytoma. In the same year, cDNA coding for a precursor peptide comprising 185 amino acids and the complete amino acid sequence of this precursor peptide were also described. The precursor peptide, which comprises, inter alia, a signal sequence of 21 amino acids at the N-terminus, is referred to as "preproadrenomedullin" (pre-proADM). Pre-proADM comprises 185 amino acids and has the sequence according to SEQ ID No: 3. The mature ADM is displayed in SEQ ID No. 4 and the mature ADM-Gly is displayed in SEQ No. 5.

The peptide adrenomedullin (ADM) is a peptide which comprises 52 amino acids (SEQ ID No: 2) and which comprises the amino acids 95 to 146 of pre-proADM, from which it is formed by proteolytic cleavage. To date, substantially only a few fragments of the peptide fragments formed in the cleavage of the pre-proADM have been more exactly characterized, in particular the physiologically active peptides adrenomedullin (ADM) and "PAMP", a peptide comprising 20 amino acids (22-41) which follows the 21 amino acids of the signal peptide in pre-proADM. For both ADM and PAMP, physiologically active sub-fragments have furthermore been discovered and investigated in more detail. The discovery and characterization of ADM in 1993 triggered intensive research activity and a flood of publications, the results of which have recently been summarized in various review articles, in the context of the present description, reference being made in particular to the articles to be found in an issue of "Peptides" devoted to ADM (Peptides 22 (2001)), in particular (2) and (3). A further review is (4). In the scientific investigations to date, it has been found, inter alia, that ADM may be regarded as a polyfunctional regulatory peptide. It is released into the circulation in an inactive form extended by glycine (5). There is also a binding protein (6) which is specific for ADM and probably likewise modulates the effect of ADM.

Those physiological effects of ADM as well as of PAMP which are of primary importance in the investigations to date were the effects influencing blood pressure. Thus, ADM is an effective vasodilator, it being possible to associate the hypotensive effect with in particular peptide segments in the C-terminal part of ADM.

It has furthermore been found that the abovementioned further physiologically active peptide PAMP formed from pre-proADM likewise exhibits a hypotensive effect, even if it appears to have an action mechanism differing from that of ADM (cf. in addition to the abovementioned review articles (3) and (4) also (7), (8) or (9) and (10)).

It has furthermore been found that the concentrations of ADM which can be measured in the circulation and other biological fluids are, in a number of pathological states, significantly above the concentrations to be found in healthy control persons. Thus, the ADM level in patients with congestive heart failure, myocardial infarction, kidney diseases, hypertensive disorders, Diabetes mellitus, in the acute phase of shock and in sepsis and septic shock are significantly increased, although to different extents. The PAMP concentrations are also increased in some of said pathological states, but the plasma levels are reduced relative to ADM ((3); page 1702).

It is furthermore known that unusually high concentrations of ADM are to be observed in sepsis or in septic shock (cf. (3) and (11), (12), (13), (14) and (15)). The findings are related to the typical hemodynamic changes which are known as typical phenomena of the course of a disease in patients with sepsis and other severe syndromes, such as, for example, SIRS.

Although it is assumed that ADM and PAMP are formed from the same precursor peptide, pre-proADM (SEQ ID No: 3), in which the amino acid sequences corresponding to these peptides are present as partial peptides in equimolar amounts, the concentrations of ADM or PAMP measurable in biological fluids apparently differ. This is nothing unusual.

Thus, the measurable concentrations of different degradation products of one and the same precursor peptide may be different, for example, because they are the result of different competing degradation pathways which, for example in the case of different pathological states, lead to different fragmentation of a precursor peptide and hence to different degradation products. Certain partial peptides contained in the precursor peptide may be formed as free peptides or may not be formed, and/or different peptides are formed in different ways and in different amounts. Even if only a single degradation pathway is taken for processing a precursor peptide, and hence all degradation products originate from one and the same precursor peptide and must have been formed per se primarily in equimolar amounts, the steady state concentrations of different partial peptides and fragments measurable in biological fluids may be very different, namely, for example, when individual ones thereof are formed at a different rate and/or have different individual stabilities (lifetimes) in the respective biological fluid, or if they are removed from circulation on the basis of different clearance mechanisms and/or at different clearance rates.

Adrenomedullin plays pivotal roles during sepsis development ((16), (17)) and in numerous acute and chronic diseases ((18), (4)).

ADM is elevated in Sepsis and prognostic for outcome in sepsis ((19), (14), (11)). Sepsis treatment follow up for early monitoring of treatment success or failure is a substantial remaining unmet clinical need.

At present there are no ADM assays suitable for routine diagnostics. The sensitivity of currently available tests to determine mature ADM is too low. Therefore, high plasma volume is needed for analysis. Further, presently available assays exhibit stability related pre-analytical limitations, for instance the samples need to be stabilized by Aprotinin.

((20), (21)). On top, some ADM assays need an extensive sample preparation before measurement (11).

Goal of the present invention is to provide an assay that is suitable as a routine method for direct measurement of mature ADM suitable for standard automated laboratory and point of care technologies.

Surprisingly, it turned out that such an assay may be used for treatment follow up in septic patients.

Subject of the present invention is an in vitro method for therapy follow-up in septic patients wherein the concentration of mature ADM 1-52 and/or mature ADM 1-52-Gly in a sample of bodily fluid of said septic patient is determined using an assay comprising two binders that bind to two different regions within the region of mature adrenomedullin and/or adrenomedullin-Gly that is amino acid 21-52-amid SEQ ID No. 1 or amino acid 21-52-Gly SEQ ID No. 2 wherein each of said regions comprises at least 4 or 5 amino acids.

In one embodiment of the invention subject is an in vitro method for therapy follow-up in septic patients wherein one of said binders binds to a region comprised within the following sequence of mature ADM and/or mature ADM 1-52-Gly:

ADM 21-32:
CTVQKLAHQIYQ  (SEQ ID No. 6)

and wherein said second of these binders binds to a region comprised within the following sequence of mature ADM and/or mature ADM 1-52-Gly:

ADM 42-52:
APRSKISPQGY  (SEQ ID No. 7)

In one embodiment of the invention the assay sensitivity of said assay is able to quantify the ADM of healthy subjects and is <10 pg/ml, preferably <40 pg/ml and more preferably <70 pg/ml.

In one embodiment of the invention said binder exhibits an binding affinity to mature ADM and/or mature ADM 1-52-Gly of at least $10^7$ $M^{-1}$, preferred $10^8$ $M^{-1}$, preferred affinity is greater than $10^9$ $M^{-1}$, most preferred greater than $10^{10}$ $M^{-1}$ A person skilled in the art knows that it may be considered to compensate lower affinity by applying a higher dose of compounds and this measure would not lead out-of-the-scope of the invention.

To determine the affinity of the antibodies to Adrenomedullin, the kinetics of binding of Adrenomedullin to immobilized antibody was determined by means of label-free surface plasmon resonance using a Biacore 2000 system (GE Healthcare Europe GmbH, Freiburg, Germany). Reversible immobilization of the antibodies was performed using an anti-mouse Fc antibody covalently coupled in high density to a CMS sensor surface according to the manufacturer's instructions (mouse antibody capture kit; GE Healthcare), (22).

In one embodiment of the invention said binder is selected from the group comprising an anti-adrenomedullin antibody or an anti-ADM antibody fragment binding to ADM or a non-Ig scaffold binding to adrenomedullin.

Therapy follow up means at least once the concentration of ADM mature 1-52 (SEQ ID No. 4) and/or mature ADM 1-52-Gly (SEQ ID No. 5) is determined in a sample, preferably more than once, preferably twice or once a day after the start of therapy.

In one embodiment of the invention it may be a so-called POC-test (point-of-care), that is a test technology which allows performing the test within less than 1 hour near the patient without the requirement of a fully automated assay system. One example for this technology is the immunochromatographic test technology.

In one embodiment of the invention such an assay is a sandwich immunoassay using any kind of detection technology including but not restricted to enzyme label, chemiluminescence label, electrochemiluminescence label, preferably a fully automated assay. In one embodiment of the invention such an assay is an enzyme labeled sandwich assay. Examples of automated or fully automated assay comprise assays that may be used for one of the following systems: Roche Elecsys®, Abbott Architect®, Siemens Centauer®, Brahms Kryptor®, Biomerieux Vidas®, Alere Triage®.

A variety of immunoassays are known and may be used for the assays and methods of the present invention, these include: radioimmunoassays ("RIA"), homogeneous enzyme-multiplied immunoassays ("EMIT"), enzyme linked immunoadsorbent assays ("ELISA"), apoenzyme reactivation immunoassay ("ARIS"), dipstick immunoassays and immuno-chromatography assays.

In one embodiment of the invention at least one of said two binders is labeled in order to be detected.

The preferred detection methods comprise immunoassays in various formats such as for instance radioimmunoassay (RIA), chemiluminescence- and fluorescence-immunoassays, Enzyme-linked immunoassays (ELISA), Luminex-based bead arrays, protein microarray assays, and rapid test formats such as for instance immunochromatographic strip tests.

In a preferred embodiment said label is selected from the group comprising chemiluminescent label, enzyme label, fluorescence label, radioiodine label.

The assays can be homogenous or heterogeneous assays, competitive and non-competitive assays. In one embodiment, the assay is in the form of a sandwich assay, which is a non-competitive immunoassay, wherein the molecule to be detected and/or quantified is bound to a first antibody and to a second antibody. The first antibody may be bound to a solid phase, e.g. a bead, a surface of a well or other container, a chip or a strip, and the second antibody is an antibody which is labeled, e.g. with a dye, with a radioisotope, or a reactive or catalytically active moiety. The amount of labeled antibody bound to the analyte is then measured by an appropriate method. The general composition and procedures involved with "sandwich assays" are well-established and known to the skilled person (23).

In another embodiment the assay comprises two capture molecules, preferably antibodies which are both present as dispersions in a liquid reaction mixture, wherein a first labelling component is attached to the first capture molecule, wherein said first labelling component is part of a labelling system based on fluorescence- or chemiluminescence-quenching or amplification, and a second labelling component of said marking system is attached to the second capture molecule, so that upon binding of both capture molecules to the analyte a measurable signal is generated that allows for the detection of the formed sandwich complexes in the solution comprising the sample.

In another embodiment, said labeling system comprises rare earth cryptates or rare earth chelates in combination with fluorescence dye or chemiluminescence dye, in particular a dye of the cyanine type.

In the context of the present invention, fluorescence based assays comprise the use of dyes, which may for instance be selected from the group comprising FAM (5- or 6-carboxyfluorescein), VIC, NED, Fluorescein, Fluoresceinisothiocyanate (FITC), IRD-700/800, Cyanine dyes, such as CY3, CY5, CY3.5, CY5.5, Cy7, Xanthen, 6-Carboxy-2',4', 7',4,7-hexachlorofluorescein (HEX), TET, 6-Carboxy-4',5'-dichloro-2',7'-dimethodyfluorescein (JOE), N,N,N',N'-Tetramethyl-6-carboxyrhodamine (TAMRA), 6-Carboxy-X-rhodamine (ROX), 5-Carboxyrhodamine-6G (R6G5), 6-carboxyrhodamine-6G (RG6), RHODAMINE, RHODAMINE GREEN, RHODAMINE RED, RHODAMINE 110, BODIPY dyes, such as BODIPY TMR, OREGON GREEN, Coumarins such as Umbelliferone, Benzimides, such as Hoechst 33258; Phenanthridines, such as TEXAS RED, YAKIMA YELLOW, ALEXA FLUOR, PET, Ethidiumbromide, Acridinium dyes, Carbazol dyes, Phenoxazine dyes, Porphyrine dyes, Polymethin dyes, and the like.

In the context of the present invention, chemiluminescence based assays comprise the use of dyes, based on the physical principles described for chemiluminescent materials in (24). Preferred chemiluminescent dyes are acridiniumesters.

As mentioned herein, an "assay" or "diagnostic assay" can be of any type applied in the field of diagnostics. Such an assay may be based on the binding of an analyte to be detected to one or more capture probes with a certain affinity. Concerning the interaction between capture molecules and target molecules or molecules of interest, the affinity constant is preferably greater than $10^8$ $M^{-1}$.

In the context of the present invention, "binder molecules" are molecules which may be used to bind target molecules or molecules of interest, i.e. analytes (i.e. in the context of the present invention PCT and fragments thereof), from a sample. Binder molecules must thus be shaped adequately, both spatially and in terms of surface features, such as surface charge, hydrophobicity, hydrophilicity, presence or absence of lewis donors and/or acceptors, to specifically bind the target molecules or molecules of interest. Hereby, the binding may for instance be mediated by ionic, van-der-Waals, pi-pi, sigma-pi, hydrophobic or hydrogen bond interactions or a combination of two or more of the aforementioned interactions between the capture molecules and the target molecules or molecules of interest. In the context of the present invention, binder molecules may for instance be selected from the group comprising a nucleic acid molecule, a carbohydrate molecule, a PNA molecule, a protein, an antibody, a peptide or a glycoprotein. Preferably, the binder molecules are antibodies, including fragments thereof with sufficient affinity to a target or molecule of interest, and including recombinant antibodies or recombinant antibody fragments, as well as chemically and/or biochemically modified derivatives of said antibodies or fragments derived from the variant chain with a length of at least 12 amino acids thereof.

Chemiluminescent label may be acridinium ester label, steroid labels involving isoluminol labels and the like.

Enzyme labels may be lactate dehydrogenase (LDH), creatinekinase (CPK), alkaline phosphatase, aspartate aminotransferace (AST), alanine aminotransferace (ALT), acid phosphatase, glucose-6-phosphate dehydrogenase and so on.

In one embodiment of the invention at least one of said two binders is bound to a solid phase as magnetic particles, and polystyrene surfaces.

In one embodiment of the invention the concentration of mature ADM 1-52 and/or mature ADM 1-52-Gly measured in the sample is in the range between 10-500 pg/ml in plasma or blood.

The ADM levels of the present invention have been determined with the described ADM assay. The above mentioned values might be different in other ADM assays, depending upon their way of calibration. The above mentioned values shall apply for such differently calibrated ADM assays accordingly, taking into account the differences in calibration. ADM assays could be calibrated by correlation and adjustment via their normal ranges (healthy population). Alternatively, commercially available control samples could be used for adjustment of different calibrations (ICI Diagnostics, Berlin, Germany) With the described ADM assay, the median of of a normal population has been determined to be 24.7 pg/mL.

In one embodiment of the invention a threshold is applied whereby a value above threshold is indicative of a patient that is not or bad responding to therapy and whereas a value below said threshold is indicative of a patient responding to therapy.

In one embodiment of the invention a threshold of 60 to 80 pg/ml, preferably 70 pg/ml is applied.

In one embodiment of the invention said sample is selected from the group comprising human citrate plasma, heparin plasma, EDTA plasma, whole blood.

In one embodiment of the invention said sample taken is directly measured without any further sample preparation.

In one embodiment of the invention said method is performed on a fully automated device. Roche Elecsys®, Abbott Architect®, Siemens Centauer®, Brahms Kryptor®, Biomerieux Vidas®, Alere Triage®.

In one embodiment of the invention mature ADM 1-52 and/or mature ADM 1-52-Gly is determined in at least two samples wherein said samples are taken in different points of time from said septic patients. Said samples may be taken once a day during days of therapy. Such diagnostic regimen may be applied that are described for other biomarker, e.g. (25) and also (26).

In one embodiment of the invention the sample volume measured is less or equal to 50 ul.

The in vitro method for therapy follow-up in septic patients according to the present invention may be combined with further clinical and/or laboratory parameters and or clinical scores such as for instance Apache 2 score, SOFA score, or others, or one or more parameters contained within the score. Variables/parameters maybe combined continuously or discontinuously using standard statistical tools.

Subject matter of the invention is further an assay for determining mature adrenomedullin and/or adrenomedullin-Gly in a sample comprising two binders that bind to two different regions within the region of mature adrenomedullin and/or adrenomedullin-Gly that is amino acid 21-52-amid SEQ ID No. 1 or amino acid 21-52-Gly of mature adrenomedullin SEQ ID No. 2 wherein each of said regions comprises at least 4 or 5 amino acids and wherein said assay is not a manual coated-tube-Acridinium ester sandwich assay.

Subject matter of the invention is further an assay for determining mature adrenomedullin and/or adrenomedullin-Gly and/or adrenomedullin-Gly in a sample comprising two binders that bind to two different regions within the region of mature adrenomedullin and/or adrenomedullin-Gly that is amino acid 21-52-amid SEQ ID No. 1 or amino acid 21-52-Gly of mature adrenomedullin SEQ ID No. 2 wherein each of said regions comprises at least 4 or 5 amino acids and wherein said assay is a manual coated-tube-Acridinium ester sandwich assay and wherein one of said binders is an antibody binding to SEQ ID No. 4 and wherein the second of said binders is an antibody binding to SEQ ID No. 7 (APRSKISPQGY-CO—NH2).

In one embodiment of the assays for determining mature adrenomedullin and/or adrenomedullin-Gly in a sample according to the present invention one of said binders binds to a region comprised within the following sequence of mature ADM:

CTVQKLAHQIYQ (SEQ ID No. 6)

and wherein said second of these binders binds to a region comprised within the following sequence of mature ADM:

APRSKISPQGY (SEQ ID No. 7)

In one embodiment of the assays for determining mature adrenomedullin and/or adrenomedullin-Gly in a sample according to the present invention the assay sensitivity of said assay is able to quantify the ADM of healthy subjects and is <10 pg/ml, preferably <40 pg/ml and more preferably <70 pg/ml.

In one embodiment of the assays for determining mature adrenomedullin and/or adrenomedullin-Gly in a sample according to the present invention said binder exhibits an binding affinity to adrenomedullin of at least $10^7$ M$^{-1}$, preferred $10^8$ M$^{-1}$, preferred affinity constant is greater than $10^9$ M$^{-1}$, most preferred greater than $10^{10}$ M$^{-1}$. A person skilled in the art knows that it may be considered to compensate lower affinity by applying a higher dose of compounds and this measure would not lead out-of-the-scope of the invention. Binding affinity may be determined as described above.

In one embodiment of the assays for determining mature adrenomedullin and/or adrenomedullin-Gly in a sample according to the present invention said binder is selected from the group comprising an anti-adrenomedullin antibody or an anti-ADM antibody fragment binding to ADM or a non-Ig scaffold binding to adrenomedullin.

In one embodiment of the assays for determining mature adrenomedullin and/or adrenomedullin-Gly in a sample according to the present invention such assay is a sandwich assay, preferably a fully automated assay. It may be an ELISA fully automated or manual. It may be a so-called PCT-test (point-of-care). Examples of automated or fully automated assay comprise assays that may be used for one of the following systems: Roche Elecsys®, Abbott Architect®, Siemens Centauer®, Brahms Kryptor®, Biomerieux Vidas®, Alere Triage®. Examples of test formats are provided above.

In one embodiment of the assays for determining mature adrenomedullin and/or adrenomedullin-Gly in a sample according to the present invention at least one of said two binders is labeled in order to be detected. Examples of labels are provided above.

In one embodiment of the assays for determining mature adrenomedullin and/or adrenomedullin-Gly in a sample according to the present invention at least one of said two binders is bound to a solid phase. Examples of solid phases are provided above.

In one embodiment of the assays for determining mature adrenomedullin and/or adrenomedullin-Gly in a sample according to the present invention said label is selected from the group comprising chemiluminescent label, enzyme label, fluorescence label, radioiodine label.

A further subject of the present invention is a kit comprising an assay according to the present invention wherein the components of said assay may be comprised in one or more container.

A further subject of the present invention is a method of calibrating an assay according to the present invention wherein binder, preferably an antibody, is used that binds to a region of at least 5 amino acids within mature adrenomedullin and/or adrenomedullin-Gly amino acids 1-16 (SEQ ID No. 8). Said binder may be an antibody or antibody fragment or non-Ig scaffold that binds to a region of at least 5 amino acids within mature adrenomedullin and/or adrenomedullin-Gly amino acids 1-16 (SEQ ID No. 8).

In one embodiment of the method of calibrating an assay according to the invention said N-terminal antibody or fragment or scaffold recognizes and binds to the N-terminal end (aa1) of mature adrenomedullin and/or adrenomedullin-Gly. This means in another preferred embodiment said anti-ADM-antibody or an anti-Adrenomendullin antibody fragment or non-Ig scaffold binds only to a region within the sequence of mature ADM if the N-terminal end of ADM is free. In said embodiment the anti-ADM-antibody or anti-Adrenomendullin antibody fragment or non-Ig scaffold would not bind to a region within the sequence of mature ADM if said sequence is comprised within pro-ADM.

Antibodies suitable for calibrating an assay according to the invention are such binders that appease the adsorptive properties of ADM. Further such a binder must be compatible to the binders used in the detection assay, e.g. said binder should not interfere with the binding of the labelled binder and the solid phase binder in case of an ELISA.

The present methods and assays are suitable for routine applications. Routine applications require in most cases that the sample volume needed should not exceed 50 ul. Routine application also requires that the pre-analytical treatments are kept to a minimum or are zero (use of routine samples like EDTA plasma, Citrate plasma). Preanalytical requirements must fit to clinical routine: minimum analyte stability (>90% recovery) shall be at room temperature at least 2 hours.

An antibody according to the present invention is a protein including one or more polypeptides substantially encoded by immunoglobulin genes that specifically binds an antigen. The recognized immunoglobulin genes include the kappa, lambda, alpha (IgA), gamma (IgG$_1$, IgG$_2$, IgG$_3$, IgG$_4$), delta (IgD), epsilon (IgE) and mu (IgM) constant region genes, as well as the myriad immunoglobulin variable region genes. Full-length immunoglobulin light chains are generally about 25 Kd or 214 amino acids in length. Full-length immunoglobulin heavy chains are generally about 50 Kd or 446 amino acid in length. Light chains are encoded by a variable region gene at the NH2-terminus (about 110 amino acids in length) and a kappa or lambda constant region gene at the COOH-terminus. Heavy chains are similarly encoded by a variable region gene (about 116 amino acids in length) and one of the other constant region genes.

The basic structural unit of an antibody is generally a tetramer that consists of two identical pairs of immunoglobulin chains, each pair having one light and one heavy chain. In each pair, the light and heavy chain variable regions bind to an antigen, and the constant regions mediate effector functions Immunoglobulins also exist in a variety of other forms including, for example, Fv, Fab, and (Fab')$_2$, as well as bifunctional hybrid antibodies and single chains ((27), (28), (29), (30), (31)). An immunoglobulin light or heavy chain variable region includes a framework region interrupted by three hypervariable regions, also called complementarity determining regions (CDR's) see (32). As noted above, the CDRs are primarily responsible for binding to an epitope of an antigen. An immune complex is an antibody, such as a monoclonal antibody, chimeric antibody, humanized antibody or human antibody, or functional antibody fragment, specifically bound to the antigen.

Chimeric antibodies are antibodies whose light and heavy chain genes have been constructed, typically by genetic engineering, from immunoglobulin variable and constant region genes belonging to different species. For example, the variable segments of the genes from a mouse monoclonal antibody can be joined to human constant segments, such as kappa and gamma 1 or gamma 3. In one example, a therapeutic chimeric antibody is thus a hybrid protein composed of the variable or antigen-binding domain from a mouse antibody and the constant or effector domain from a human antibody, although other mammalian species can be used, or the variable region can be produced by molecular techniques. Methods of making chimeric antibodies are well known in the art, e.g., see (33). A "humanized" immunoglobulin is an immunoglobulin including a human framework region and one or more CDRs from a non-human (such as a mouse, rat, or synthetic) immunoglobulin. The non-human immunoglobulin providing the CDRs is termed a "donor" and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Exemplary conservative substitutions are those such as gly, ala; val, ile, leu; asp, glu; asn, gln; ser, thr; lys, arg; and phe, tyr. Humanized immunoglobulins can be constructed by means of genetic engineering (e.g., see (34)). A human antibody is an antibody wherein the light and heavy chain genes are of human origin. Human antibodies can be generated using methods known in the art. Human antibodies can be produced by immortalizing a human B cell secreting the antibody of interest Immortalization can be accomplished, for example, by EBV infection or by fusing a human B cell with a myeloma or hybridoma cell to produce a trioma cell. Human antibodies can also be produced by phage display methods (see, e.g., (35), (36), (37), which are herein incorporated by reference), or selected from a human combinatorial monoclonal antibody library (see the Morphosys website). Human antibodies can also be prepared by using transgenic animals carrying a human immunoglobulin gene (for example, see (38) and (39) which are herein incorporated by reference).

Thus, the ADM antibody may have the formats known in the art. Examples are human antibodies, monoclonal antibodies, humanized antibodies, chimeric antibodies, CDR-grafted antibodies. In a preferred embodiment antibodies according to the present invention are recombinantly produced antibodies as e.g. IgG, a typical full-length immunoglobulin, or antibody fragments containing at least the F-variable domain of heavy and/or light chain as e.g. chemically coupled antibodies (fragment antigen binding) including but not limited to Fab-fragments including Fab minibodies, single chain Fab antibody, monovalent Fab antibody with epitope tags, e.g. Fab-V5Sx2; bivalent Fab (miniantibody) dimerized with the CH3 domain; bivalent Fab or multivalent Fab, e.g. formed via multimerization with the aid of a heterologous domain, e.g. via dimerization of dHLX domains, e.g. Fab-dHLX-FSx2; F(ab')2-fragments, scFv-fragments, multimerized multivalent or/and multispecific scFv-fragments, bivalent and/or bispecific diabodies, BITE® (bispecific T-cell engager), trifunctional antibodies, polyvalent antibodies, e.g. from a different class than G; single-domain antibodies, e.g. nanobodies derived from camelid or fish immunoglobulines and numerous others.

In addition to anti-ADM antibodies other biopolymer scaffolds are well known in the art to complex a target molecule and have been used for the generation of highly target specific biopolymers. Examples are aptamers, spiegelmers, anticalins and conotoxins.

In a preferred embodiment the ADM antibody format is selected from the group comprising Fv fragment, scFv fragment, Fab fragment, scFab fragment, (Fab)2 fragment and scFv-Fc Fusion protein. In another preferred embodiment the antibody format is selected from the group comprising scFab fragment, Fab fragment, scFv fragment and bioavailability optimized conjugates thereof, such as PEGylated fragments. One of the most preferred formats is the scFab format.

Non-Ig scaffolds may be protein scaffolds and may be used as antibody mimics as they are capable to bind to ligands or antigenes. Non-Ig scaffolds may be selected from the group comprising tetranectin-based non-Ig scaffolds (e.g. described in (40), fibronectin scaffolds (e.g. described in (41); lipocalin-based scaffolds ((e.g. described in (42)); ubiquitin scaffolds (e.g. described in (43)), transferring scaffolds (e.g. described in (44)), protein A scaffolds (e.g. described in (45)), ankyrin repeat based scaffolds (e.g. described in (46), microproteins preferably microproteins forming a cystine knot) scaffolds (e.g. described in (47)), Fyn SH3 domain based scaffolds (e.g. described in (48) EGFR-A-domain based scaffolds (e.g. described in (49)) and Kunitz domain based scaffolds (e.g. described in (59)).

In another preferred embodiment the anti-ADM antibody or the antibody fragment binding to ADM is a monospecific antibody. Monospecific antibodies are antibodies that all have affinity for the same antigen. Monoclonal antibodies are monospecific, but monospecific antibodies may also be produced by other means than producing them from a common germ cell.

In one preferred embodiment of the invention antibodies according to the present invention may be produced as follows:

A Balb/c mouse was immunized with 100 μg ADM-Peptide-BSA-Conjugate at day 0 and 14 (emulsified in 100 μl complete Freund's adjuvant) and 50 μg at day 21 and 28 (in 100 μl incomplete Freund's adjuvant). Three days before the fusion experiment was performed, the animal received 50 μg of the conjugate dissolved in 100 μl saline, given as one intraperitoneal and one intra venous injection.

Splenocytes from the immunized mouse and cells of the myeloma cell line SP2/0 were fused with 1 ml 50% polyethylene glycol for 30 s at 37° C. After washing, the cells were seeded in 96-well cell culture plates. Hybrid clones were selected by growing in HAT medium [RPMI 1640 culture medium supplemented with 20% fetal calf serum and HAT-Supplement]. After two weeks the HAT medium is replaced with HT Medium for three passages followed by returning to the normal cell culture medium.

The cell culture supernatants were primary screened for antigen specific IgG antibodies three weeks after fusion. The positive tested microcultures were transferred into 24-well plates for propagation. After retesting the selected cultures were cloned and recloned using the limiting-dilution technique and the isotypes were determined (see also (51) and (52)).

Antibodies may be produced by means of phage display according to the following procedure: The human naive antibody gene libraries HAL7/8 were used for the isolation of recombinant single chain F-Variable domains (scFv) against adrenomedullin peptide. The antibody gene libraries were screened with a panning strategy comprising the use of peptides containing a biotin tag linked via two different spacers to the adrenomedullin peptide sequence. A mix of panning rounds using non-specifically bound antigen and streptavidin bound antigen were used to minimize background of non-specific binders. The eluted phages from the third round of panning have been used for the generation of monoclonal scFv expressing *E. coli* strains. Supernatant from the cultivation of these clonal strains has been directly used for an antigen ELISA testing. (53) and (54).

Humanization of murine antibodies may be conducted according to the following procedure: For humanization of an antibody of murine origin the antibody sequence is analyzed for the structural interaction of framework regions (FR) with the complementary determining regions (CDR) and the antigen. Based on structural modeling an appropriate FR of human origin is selected and the murine CDR sequences are transplanted into the human FR. Variations in the amino acid sequence of the CDRs or FRs may be introduced to regain structural interactions, which were abolished by the species switch for the FR sequences. This recovery of structural interactions may be achieved by random approach using phage display libraries or via directed approach guided by molecular modeling (55.)

Development of Antibodies

We developed mouse monoclonal antibodies binding to the N-terminal, mid-regional and C-terminal part of hADM and their affinity constants were determined (table 1).

Peptides for Immunization

Peptides were supplied by JPT Peptide Technologies GmbH (Berlin, Germany). Peptides were coupled to BSA using the Sulfo-SMCC crosslinking method. The crosslinking procedure was performed according the manufacturers instructions (Thermo Fisher/Pierce).

EXAMPLE 1

Generation of Antibodies and Determination of their Affinity Constants

The murine antibodies were generated according to the following method:

A Balb/c mouse was immunized with 100 µg Peptide-BSA-Conjugate at day 0 and 14 (emulsified in 100 µl complete Freund's adjuvant) and 50 µg at day 21 and 28 (in 100 µl incomplete Freund's adjuvant). Three days before the fusion experiment was performed, the animal received 50 µg of the conjugate dissolved in 100 µl saline, given as one intraperitoneal and one intra venous injection.

Splenocytes from the immunized mouse and cells of the myeloma cell line SP2/0 were fused with 1 ml 50% polyethylene glycol for 30 s at 37° C. After washing, the cells were seeded in 96-well cell culture plates. Hybrid clones were selected by growing in HAT medium [RPMI 1640 culture medium supplemented with 20% fetal calf serum and HAT-Supplement]. After two weeks the HAT medium is replaced with HT Medium for three passages followed by returning to the normal cell culture medium.

The cell culture supernatants were primary screened for antigen specific IgG antibodies three weeks after fusion. The positive tested microcultures were transferred into 24-well plates for propagation. After retesting the selected cultures were cloned and recloned using the limiting-dilution technique and the isotypes were determined. ((51) and (52)).

TABLE 1

| Antigen/Immunogen | ADM Region | Designation | Affinity constants Kd ($M^{-1}$) |
|---|---|---|---|
| YRQSMNNFQGLRSFGC | 1-16 | NT-ADM | $1.6 \times 10^9$ |
| CTVQKLAHQIYQ | 21-32 | MR-ADM | $2 \times 10^9$ |
| CAPRS KISPQGY-NH2 | C-42-52 | CT-ADM | $1.1 \times 10^9$ |

Monoclonal Antibody Production

Antibodies were produced via standard antibody production methods (56) and purified via Protein A. The antibody purities were >95% based on SDS gel electrophoresis analysis.

Affinity Constants

To determine the affinity of the antibodies to Adrenomedullin, the kinetics of binding of Adrenomedullin to immobilized antibody was determined by means of label-free surface plasmon resonance using a Biacore 2000 system (GE Healthcare Europe GmbH, Freiburg, Germany). Reversible immobilization of the antibodies was performed using an anti-mouse Fc antibody covalently coupled in high density to a CM5 sensor surface according to the manufacturer's instructions (mouse antibody capture kit; GE Healthcare). (22)

Labelling procedure (tracer): 100 ug (100 ul) of antibody (1 mg/ml in PBS, pH 7.4,) was mixed with 10 ul Acridinium NHS-ester (1 mg/ml in acetonitrile, InVent GmbH, Germany) (57) and incubated for 20 min at room temperature. Labelled CT-H was purified by Gel-filtration HPLC on Bio-Sil® SEC 400-5 (Bio-Rad Laboratories, Inc., USA) The purified labeled antibody was diluted in (300 mmol/L potassiumphosphate, 100 mmol/L NaCl, 10 mmol/L Na-EDTA, 5 g/L Bovine Serum Albumin, pH 7.0). The final concentration was approx. 800.000 relative light units (RLU) of labelled compound (approx. 20 ng labeled antibody) per 200

µL. Acridinium ester chemiluminescence was measured by using an AutoLumat LB 953 (Berthold Technologies GmbH & Co. KG).

Solid phase: Polystyrene tubes (Greiner Bio-One International AG, Austria) were coated (18 h at room temperature) with antibody ((1.5 µg antibody/0.3 mL 100 mmol/L NaCl, 50 mmol/L TRIS/HCl, pH 7.8). After blocking with 5% bovine serum albumine, the tubes were washed with PBS, pH 7.4 and vacuum dried.

Calibrators:

Synthetic human ADM (Bachem, Switzerland) was linearly diluted using 50 mM Tris/HCl, 250 mM NaCl, 0.2% TRITON X-100, which is 2-[4-(2,4,4-trimethylpentan-2-yl)phenoxy]ethanol, 0.5% BSA, 20 tabs/L Protease cOmplete Protease Inhibitor Cocktail Tablets (Roche AG); pH 7.8. Calibrators were stored at −20° C. before use.

EXAMPLE 2

Determination of the Antibody Combination that Yields High Signal/Noise Ratios hADM Immunoassay:

50 ul of sample (or calibrator) was pipetted into coated tubes, after adding labeled second antibody (200 ul), the tubes were incubated for 2 h at room temperature. Unbound tracer was removed by washing 5 times (each 1 ml) with washing solution (20 mM PBS, pH 7.4, 0.1% TRITON X-100, which is 2-[4-(2,4,4-trimethyl-pentan-2-yl)phenoxyl ethanol).

Tube-bound chemiluminescence was measured by using the LB 953

All antibodies were used in a sandwich immunoassay as coated tube and labeled antibody and combined in the following variations (table 2):

Incubation was performed as described under hADM-Immunoassay. Results are given in ratio of specific signal (at 10 ng/ml ADM)/background (sample without ADM) signal,

TABLE 2

| Signal/noise ratio | NT-ADM tracer | MR-ADM tracer | CT-ADM tracer |
|---|---|---|---|
| NT-ADM | / | 195 | 241 |
| MRADM | 204 | / | 904 |
| CT-ADM | 260 | 871 | / |

Surprisingly, we found the combination of MR-ADM and CT-ADM as combination for highest signal/noise ratio.

Subsequently, we used this antibody-combination for further investigations. We used MR-ADM as solid phase antibody and CT-ADM as labeled antibody. A typical dose/signal curve is shown in FIG. 1. The analytical sensitivity (average of 10 runs, ADM-free sample+2SD) of the assay was 2 pg ADM/ml.

EXAMPLE 3

Stability of Human Adrenomedullin:

Human ADM was diluted in human Citrate plasma (n=5, final concentration 10 ng ADM/ml) and incubated at 24° C. At selected time points, aliquots were frozen at −20° C. Immediately after thawing the samples hADM was quantified by using the hADM immunoassay described above.

Table 3 shows the stability of hADM in human plasma at 24° C.

| Time (h) | Average ADM recovery (N = 5) | Relative loss of immune reactivity | Loss of immune reactivity %/h |
|---|---|---|---|
| 0 | 100 | / | / |
| 2 | 99.2 | 0.8 | 0.4 |
| 4 | 96.4 | 3.6 | 0.8 |
| 8 | 88.2 | 11.8 | 1.5 |
|  |  |  | Average: 0.9%/h |

Surprisingly, using the antibody-combinations MR-ADM and CT-ADM in a sandwich immune assay, the preanalytical stability of the analyte is high (only 0.9%/h average loss of immune reactivity). In contrast, using other assay methods, a plasma half life of only 22 min was reported (Hinson 2000). Since the time from taking sample to analysis in hospital routine is less than 2 h, the used ADM detection method is suitable for routine diagnosis. It is remarkable, that any non routine additives to samples (like Aprotinin, (20)) are not needed to reach acceptable ADM-immune reactivity stabilities.

EXAMPLE 4

Reproducibility of Calibrator-Preparations.

We found a high variation of results, preparing calibrators for ADM assays (average CV 8.5%, see table 4). This may be due to high adsorption of hADM to plastic and glass surfaces (see also (58)). This effect was only slightly reduced by adding detergents (up to 1% TRITON X 100, which is 2-[4-(2,4,4-trimethylpentan-2-yl)phenoxy]ethanol, or 1% TWEEN 20, which is polyoxyethylene (20) sorbitan monolaurate), protein (up to 5% BSA) and high ionic strength (up to 1M NaCl) or combinations thereof. Surprisingly, if a surplus of anti ADM antibody (10 ug/ml) is added to the calibrator dilution buffer, the recovery and reproducibility of ADM assay calibrator-preparations was substantially improved to <1% of inter preparation CV (table 4).

Fortunately, the presence of N-terminal antibodies did not effect the ADM-signal generated by the combination of MR- and C-terminal antibodies (FIG. 11).

TABLE 4

| calibrator | In the presence of NT-ADM antibody (10 ug/ml) | Inter preparation CV (%) | Without antibody | Inter preparation CV (%) |
|---|---|---|---|---|
| 100 ng/ml | 3453 s/n-r | 0.9 | 2842 s/n-r | 2.8 |
| 10 ng/ml | 1946 s/n-r | 0.8 | 1050 s/n-r | 7.9 |
| 1 ng/ml | 179 s/n-r | 1.1 | 77 s/n-r | 14.8 |
|  |  | Average: 0.93 |  | Average: 8.5 |

Inter preparation variation of calibrators.

ADM assay calibrators were prepared as described above with and without 10 ug/ml of NT-ADM-antibody. Coeffients of variation are given from 5 independent preparation runs. The calibrators were measured using the ADM assay described above. s/n-r=signal to noise ratio.

For all following studies, we used an ADM assay, based on calibrators, prepared in the presence of 10 ug/ml of NT-ADM antibody and 10 ug/ml of NT-ADM antibody as supplement in the tracer buffer.

EXAMPLE 5

Sensitivity

The goal of assay sensitivity was to completely cover the ADM concentration of healthy subjects.

ADM concentration in healthy subjects:

Healthy subjects (n=100, average age 56 years) were measured using the ADM assay. The median value was 24.7 pg/ml, the lowest value 11 pg/ml and the 99$^{th}$ percentile 43 pg/ml. Since the assay sensitivity was 2 pg/ml, 100% of all healthy subjects were detectable using the described ADM assay (see FIG. 2).

EXAMPLE 6

Clinical Study

101 ED patients fulfilling the definition of sepsis (59) were subsequently hospitalized (average 5 days of hospitalization) and received a standard of care treatment. EDTA-plasma was generated from day 1 (ED presentation) and one sample each day during hospital stay. The time to freeze samples for later ADM-measurement was less than 4 h.

Patient characteristics are summarized in table 5

TABLE 5

| Variable | all (n = 101) | in hospital deaths (n = 27) | discharged (n = 74) | p-value |
|---|---|---|---|---|
| Demographics | | | | |
| Gender - male | 60 (60) | 13 (48) | 47 (64) | 0.163 |
| Age - median [IQR] | 78 [72-72] | 77 [71.25-83] | 80 [75-84.5] | 0.142 |
| Examination variables | | | | |
| BP systolic (mmHg) - median [IQR] | 115 [100-100] | 120 [106.25-138.75] | 105 [80-120] | 0.001 |
| BP diastolic (mmHg) - median [IQR] | 65 [60-60] | 65 [60-85] | 60 [50-70] | 0.002 |
| HR - median [IQR] | 100 [94-94] | 100 [94-114.75] | 100 [93.5-107.5] | 0.407 |
| RR - median [IQR] | 24 [22-22] | 24 [22-28] | 26 [24-28] | 0.069 |
| MAP (mmHg) - median [IQR] | 83.3 [74-74] | 83.3 [77.62-100.75] | 81.6 [63.5-89] | 0.026 |
| concomitant diseases | | | | |
| Cardiovascular - yes | 26 (25.7) | 9 (33.3) | 17 (23) | 0.311 |
| Hypertensive - yes | 47 (46.5) | 13 (48.1) | 34 (45.9) | 1.000 |
| Diabetes - yes | 35 (34.7) | 9 (33.3) | 26 (35.1) | 1.000 |
| Cancere - yes | 13 (12.9) | 3 (11.1) | 10 (13.5) | 1.000 |
| routine laboratory variables | | | | |
| Blood culture - yes | 31 (31) | 5 (19) | 26 (35) | 0.246 |
| negative | 15 (16.3) | 2 (8) | 13 (19.4) | |
| positive | 16 (17.4) | 3 (12) | 13 (19.4) | |
| Creatinine clearance (ml/min) - median [IQR] | 48 [23.25-23.25] | 56 [29.25-80] | 31.5 [14.75-66] | 0.043 |
| Creatinine - median [IQR] | 1.3 [0.9-0.9] | 1.25 [0.9-2.08] | 1.8 [1-3.15] | 0.080 |
| UREA - median [IQR] | 36 [21-21] | 31.5 [20-53.25] | 51 [42-87] | 0.004 |
| GCS - median [IQR] | 15 [10-10] | 15 [12.5-15] | 8 [8-11] | <0.001 |
| Pcr - median [IQR] | 16 [6.6-6.6] | 14.5 [6.7-23.7] | 17.35 [6.6-28.05] | 0.846 |
| Gluco - median [IQR] | 113.5 [94.5-94.5] | 110 [95.5-144] | 128 [94-160.5] | 0.400 |
| biliru - median [IQR] | 0.9 [0.71-0.71] | 0.9 [0.7-1.03] | 0.91 [0.77-1.18] | 0.534 |
| GR - median [IQR] | 3.8 [3.3-3.3] | 3.8 [3.2-4.3] | 3.7 [3.4-4.2] | 0.684 |
| GB - median [IQR] | 12700 [6774-6774] | 13100 [8115-17565] | 11920 [25.55-18790] | 0.343 |
| PLT - median [IQR] | 213 [150-150] | 217 [154.75-301] | 185 [130-236.5] | 0.113 |
| HCT - median [IQR] | 32 [28-28] | 31.5 [28-37] | 34 [31.25-39.5] | 0.149 |
| Leuco/Neutr (%) - median [IQR] | 87 [80-80] | 86 [78.25-89.95] | 91 [87-93.05] | 0.001 |
| HB - median [IQR] | 10.4 [9.47-9.47] | 10.15 [9.3-12.4] | 10.85 [9.9-12.67] | 0.220 |
| Na - median [IQR] | 137 [134-134] | 137 [133-141] | 139 [134-144.5] | 0.204 |
| K - median [IQR] | 3.9 [3.5-3.5] | 3.9 [3.6-4.3] | 3.9 [3.3-5.1] | 0.982 |
| INR - median [IQR] | 1.19 [1.1-1.1] | 1.19 [1.1-1.4] | 1.18 [1.04-1.36] | 0.731 |
| TC - median [IQR] | 38.4 [36-36] | 38.5 [38.12-38.7] | 36 [35.55-38.5] | <0.001 |
| SAO2 - median [IQR] | 94 [90-90] | 95 [90.25-97] | 93 [88.5-95.5] | 0.119 |
| pH - median [IQR] | 7.45 [7.38-7.38] | 7.46 [7.4-7.5] | 7.4 [7.24-7.4] | <0.001 |
| PO2 - median [IQR] | 67 [56-56] | 66.5 [56-78] | 67 [56.5-79.5] | 0.806 |
| PCO2 - median [IQR] | 36 [32-32] | 37.5 [33-43.75] | 34 [30-41] | 0.245 |
| Lact - median [IQR] | 1.5 [1-1] | 1.3 [0.83-1.9] | 2.5 [1.4-4.15] | <0.001 |
| Bic - median [IQR] | 23.5 [21-21] | 24.25 [21.43-28] | 21 [17.35-23.25] | 0.001 |
| FiO2 (%) - median [IQR] | 21 [21-21] | 21 [21-23.25] | 24 [21-45] | <0.001 |
| other | | | | |
| Acute organ disfunction - yes | 39 (43.3) | 16 (64) | 23 (35.4) | 0.021 |
| Apache score (%) - median [IQR] | 19 [12.5-12.5] | 14.65 [12.12-20.38] | 32 [20-39] | <0.001 |
| Days hospitalized - median [IQR] | 5 [2-2] | 6 [4-7] | 2 [1-6] | 0.003 |
| treatment at baseline | | | | |
| Diuresis (cc) - median [IQR] | 900 [600-600] | 1000 [700-1200] | 450 [200-1025] | <0.001 |
| Steroids - yes | 16 (15.8) | 4 (14.8) | 12 (16.2) | 1.000 |
| Vasopressors - yes | 18 (17.8) | 13 (48.1) | 5 (6.8) | <0.001 |

TABLE 5-continued

| Variable | all (n = 101) | in hospital deaths (n = 27) | discharged (n = 74) | p-value |
|---|---|---|---|---|
| Antibiotics - yes | 101 (100) | 27 (100) | 74 (100) | 1.000 |
| Fluid therapy - yes | 101 (100) | 27 (100) | 74 (100) | 1.000 |
| new biomarker | | | | |
| ADM (pg/mL) - median [IQR] | 53.8 [37.4-94.0] | 93.9 [48.7-241] | 50.1 [32.2-77.5] | <0.001 |

26.7% of all patients died during hospital stay and are counted as treatment non responder, 73.3% of all patients survived the sepsis and are counted as treatment responder.

66% off all patients presenting with sepsis had a non-normal ADM value >43 pg/ml ($99^{th}$ percentile), indicating ADM not to be a marker for the infection.

Results of Clinical Study

Initial ADM is highly prognostic.

We correlated the initial ADM value with the in hospital mortality and compared ADM with APACHE 2 sepsis score (see (60)). ADM is highly prognostic for sepsis outcome (see FIG. 3) and comparable to APACHE 2 score. There is a significant added information if ADM and APACHE 2 are combined (FIG. 4).

ADM in treatment monitoring.

Patients were treated based on standard of care treatments (table 5). The average hospitalization time was 5 days. ADM was measured each day in hospital (day 1=admission) and correlated to in hospital mortality (table 6). ADM changed during hospital stay and the change during time improved the prognostic value by 52% from initial Chit of 19.2 to 29.2 on day 5.

Using a simple cut off model at 70 pg/ml of ADM showed a 68% risk of death for patients starting at ADM concentrations >70 pg/ml and remain all the hospital stay >70 pg/ml (treatment non-responder). Patients having all time an ADM value <70 pg/ml or developing from >70 pg/ml to <70 pg/ml had a mortality of only 11% (well treated/treatment responder) and patients presenting with ADM values >70 pg/ml and reducing their ADM concentration during hospital treatment to values <70 pg/ml had a 0% mortality. There were no patients developing from <70 pg/ml to >70 pg/ml during hospital treatment. The average time needed to generate responder/nonresponder information for all patients was about 1 day. The >70 pg/ml-patients responding to treatment during hospital stay needed about 2 days to indicate treatment success by ADM.

TABLE 6

| | Patient all days >70 pg/ml | Patient all days <70 pg/ml | Patients changed from >70 pg/ml to <70 pg/ml |
|---|---|---|---|
| n | 28/101 (27.7%) | 73/101 (72.3%) | 15/73 (20.5%) |
| Mortality | 68% | 11% | 0% |
| Average days after hospitalization of change from ADM >70 pg/ml to ADM <70 pg/ml or no change | 1 day | 1.2 days | 2.2 days |

LITERATURE (1) Kitamura, K., et al., "Adrenomedullin: A Novel Hypotensive Peptide Isolated From Human Pheochromocytoma", Biochemical and Biophysical Research Communications, Vol. 192 (2), pp. 553-560 (1993).

(2) Editorial, Takahashi, K., "Adrenomedullin: from a pheochromocytoma to the eyes", Peptides, Vol. 22, p. 1691 (2001).

(3) Eto, T., "A review of the biological properties and clinical implications of adrenomedullin and proadrenomedullin N-terminal 20 peptide (PAMP), hypotensive and vasodilating peptides", Peptides, Vol. 22, pp. 1693-1711 (2001).

(4) Hinson, et al., "Adrenomedullin, a Multifunctional Regulatory Peptide", Endocrine Reviews, Vol. 21(2), pp. 138-167 (2000).

(5) Kitamura, K., et al., "The intermediate form of glycine-extended adrenomedullin is the major circulating molecular form in human plasma", Biochem. Biophys. Res. Commun., Vol. 244(2), pp. 551-555 (1998). Abstract Only.

(6) Pio, R., et al., "Complement Factor H is a Serum-binding Protein for Adrenomedulli, and the Resulting Complex Modulates the Bioactivities of Both Partners", The Journal of Biological Chemistry, Vol. 276(15), pp. 12292-12300 (2001).

(7) Kuwasako, K., et al., "Purification and characterization of PAMP-12 (PAMP-20) in porcine adrenal medulla as a major endogenous biologically active peptide", FEBS Lett, Vol. 414(1), pp. 105-110 (1997). Abstract Only.

(8) Kuwasaki, K., et al., "Increased plasma proadrenomedullin N-terminal 20 peptide in patients with essential hypertension", Ann. Clin. Biochem., Vol. 36 (Pt. 5), pp. 622-628 (1999). Abstract Only.

(9) Tsuruda, T., et al., "Secretion of proadrenomedullin N-terminal 20 peptide from cultured neonatal rat cardiac cells", Life Sci., Vol. 69(2), pp. 239-245 (2001). Abstract Only.

(10) EP 0 622 458 A2

(11) Hirata, et al., "Increased Circulating Adrenomedullin, a Novel Vasodilatory Peptide, in Sepsis", Journal of Clinical Endocrinology and Metabolism, Vol. 81(4), pp. 1449-1453 (1996).

(12) Ehlenz, K., et al., "High levels of circulating adrenomedullin in severe illness: Correlation with C-reactive protein and evidence against the adrenal medulla as site of origin", Exp Clin Endocrinol Diabetes, Vol. 105, pp. 156-162 (1997).

(13) Tomoda, Y., et al., "Regulation of adrenomedullin secretion from cultured cells", Peptides, Vol. 22, pp. 1783-1794 (2001).

(14) Ueda, S., et al., "Increased Plasma Levels of Adrenomedullin in Patients with Systemic Inflammatory Response Syndrome", Am. J. Respir. Crit. Care Med., Vol. 160, pp. 132-136 (1999).

(15) Wang, P., "Andrenomedullin and cardiovascular responses in sepsis", Peptides, Vol. 22, pp. 1835-1840 (2001).

(16) Wang 1998

(17) Wang 1998 Arch Surg, Itoh, 2007
(18) Parlapiano, C., et al.; "Adrenomedulin assay and its clinical significance", European Review for Medical and Pharmacological Sciences, 1999; 3:53-61
(19) Hirata 2007
(20) Ohta 1999
(21) Kitamura 1994
(22) Lorenz et al., "Functional Antibodies Targeting IsaA of *Staphylococcus aureus* Augment Host Immune Response and Open New Perspectives for Antibacterial Therapy"; Antimicrob Agents Chemother. 2011 January; 55(1): 165-173.
(23) The Immunoassay Handbook, Ed. David Wild, Elsevier LTD, Oxford; 3rd ed. (May 2005), ISBN-13: 978-0080445267; Hultschig C et al., Curr Opin Chem Biol. 2006 February; 10(1):4-10. PMID: 16376134
(24) Kirk-Othmer, Encyclopedia of chemical technology, 4th ed., executive editor, J. I. Kroschwitz; editor, M. Howe-Grant, John Wiley & Sons, 1993, vol. 15, p. 518-562, incorporated herein by reference, including citations on pages 551-562.
(25) Schuetz P, et al. PCT follow up measurement for monitoring antibiotic treatment success; 8Cochrane Database Syst Rev. 2012 Sep. 12; 9:CD007498. Procalcitonin to initiate or discontinue antibiotics in acute respiratory tract infections.
(26) Christ-Crain M, et al. "Procalcitonin guidance of antibiotic therapy in community-acquired pneumonia: a randomized trial" Am J Respir Crit Care Med. 2006 Jul. 1; 174(1):84-93. Epub 2006 Apr. 7.
(27) Lanzavecchia et al., Eur. J. Immunol. 17:105, 1987;
(28) Huston et al., Proc. Natl. Acad. Sci. U.S.A., 85:5879-5883, 1988;
(29) Bird et al., Science 242:423-426, 1988;
(30) Hood et al., Immunology, Benjamin, N.Y., 2nd ed., 1984;
(31) Hunkapiller and Hood, Nature 323:15-16, 1986)
(32) E. Kabat et al., Sequences of Proteins of Immunological Interest, U.S. Department of Health and Human Services, 1983
(33) U.S. Pat. No. 5,807,715.
(34) U.S. Pat. No. 5,585,089
(35) Dower et al., PCT Publication No. WO91/17271;
(36) McCafferty et al., PCT Publication No. WO92/001047;
(37) Winter, PCT Publication No. WO92/20791
(38) Lonberg et al., PCT Publication No. WO93/12227; and
(39) Kucherlapati, PCT Publication No. WO91/10741,
(40) US 2010/0028995
(41) EP 1266 025;
(42) WO 2011/154420
(43) WO 2011/073214
(44) US 2004/0023334
(45) EP 2231860
(46) WO 2010/060748
(47) EP 2314308
(48) WO 2011/023685
(49) WO 2005/040229
(50) EP 1941867
(51) Lane, R. D. (1985). A short-duration polyethylene glycol fusiontechnique for increasing production of monoclonal antibody-secreting hybridomas. J. Immunol. Meth. 81: 223-228;
(52) Ziegler, B. et al. (1996) Glutamate decarboxylase (GAD) is not detectable on the surface of rat islet cells examined by cytofluorometry and complement-dependent antibody-mediated cytotoxicity of monoclonal GAD antibodies, Horm. Metab. Res. 28: 11-15).
(53) Hust, M., et al. 2011. A human scFv antibody generation pipeline for proteome research. Journal of Biotechnology 152, 159-170;
(54) Schütte, M., et al. 2009. Identification of a putative Crf splice variant and generation of recombinant antibodies for the specific detection of *Aspergillus fumigatus*. PLoS One 4, e6625)
(55) Almagro J C, Fransson J., 2008. Humanization of antibodies. Front Biosci. 2008 Jan. 1; 13:1619-33.
(56) Marx et al., Monoclonal Antibody Prodcution, ATLA 25, 121, 1997
(57) EP 0 353 971
(58) Lewis, L., et al., "Adrenomedullin (1-52) measured in human plasma by radioimmunoassay: plasma concentration, adsorption, and storage", Clinical Chemistry, Vol. 44(3), pp. 571-577 (1998).
(59) Crit Care Med. 2008 January; 36(1):296-327.
(60) Knaus et al., 1985, 2001

BRIEF DESCRIPTION OF THE DRAWINGS

FIG. 5 and FIG. 6: Survivors, ADM is <70 pg/ml at ED presentation (day 1) and during hospital stay. ADM indicates a well treated patient.

FIG. 7 and FIG. 8: Survivors, ADM is above 70 pg/ml at ED presentation (day 1) and is lowered during hospital treatment to values below 70 pg/ml (treatment responder).

FIG. 9 and FIG. 10: Deceased patients, ADM is above 70 pg/ml at ED presentation (day 1) and is not lowered to values below 70 pg/ml during hospital treatment (treatment non responder).

Figure 1:
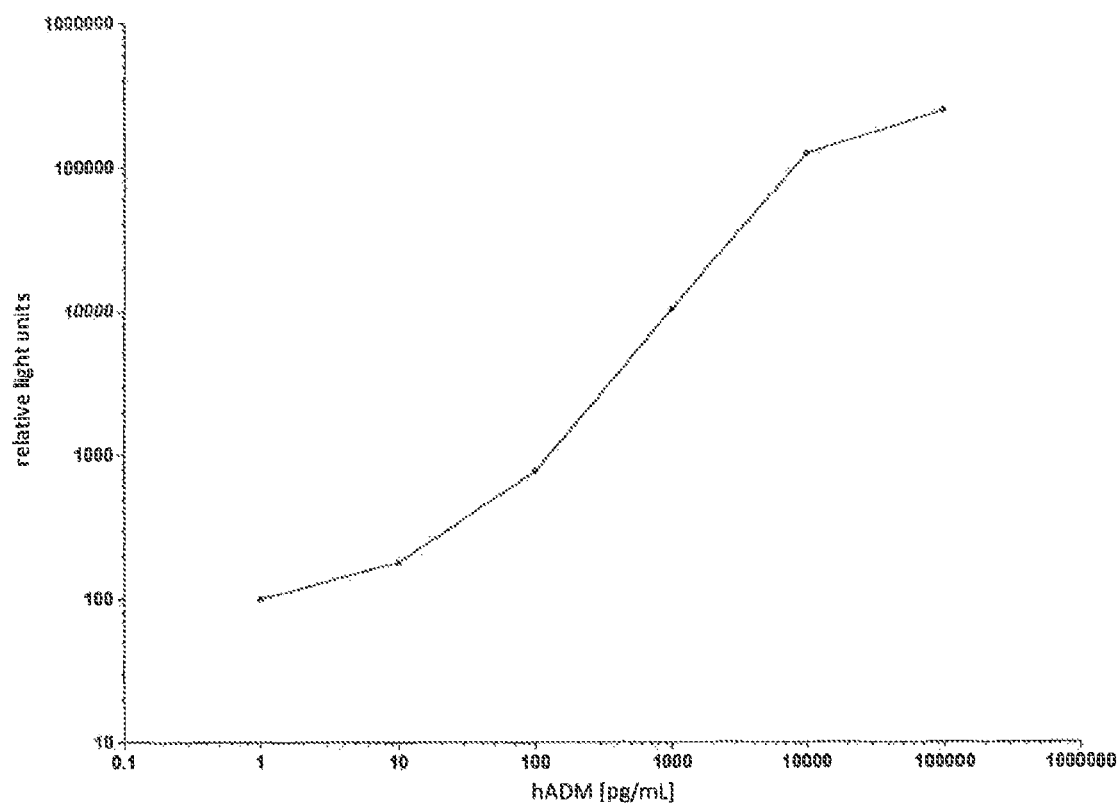
FIG. 1 shows a typical hADM dose/response curve using MR-ADM as solid phase antibody and CT-ADM as labeled antibody.
Figure 2:
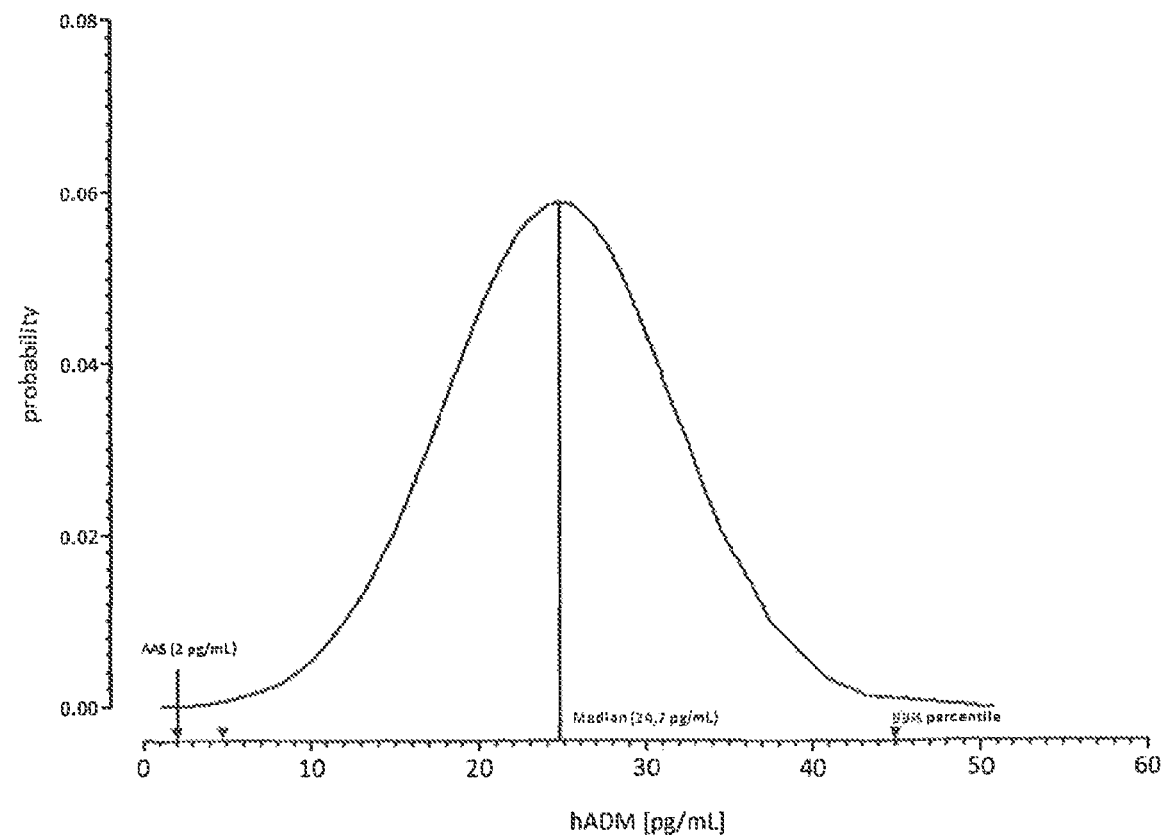
FIG. 2: Healthy subjects (n=100, average age 56 years) were measured using the ADM assay. The median value was 24.7 pg/ml, the lowest value 11 pg/ml and the $99^{th}$ percentile 43 pg/ml. Since the assay sensitivity was 2 pg/ml, 100% of all healthy subjects were detectable using the described ADM assay
Figure 3:
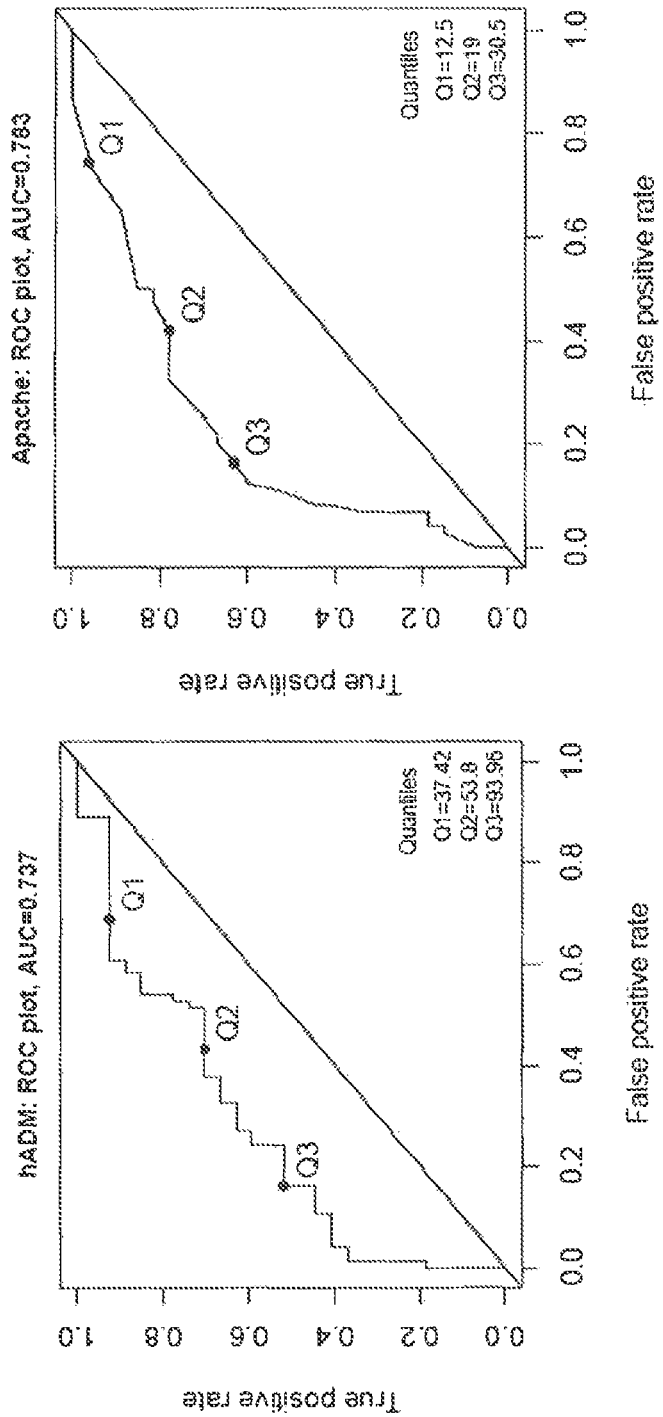
FIG. 3: Predicting in-hospital mortality—Results from logistic regression
Figure 4:
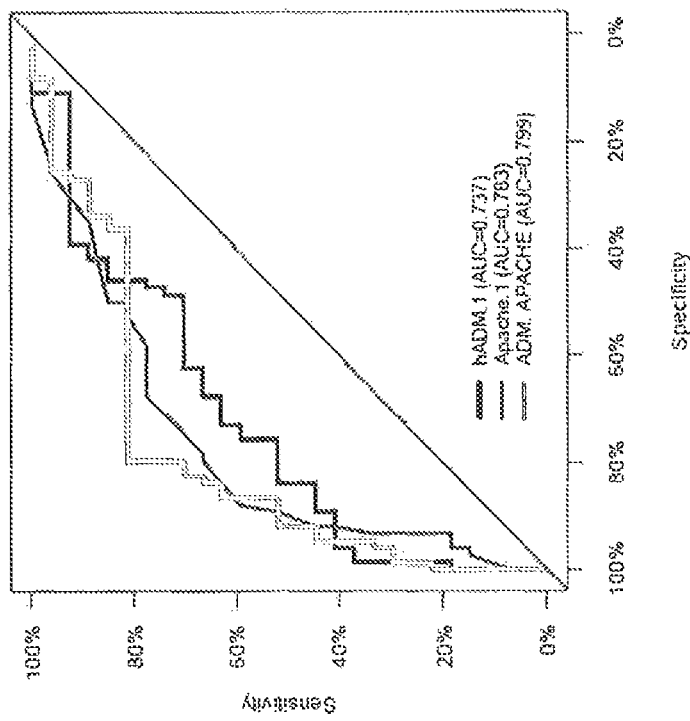
FIG. 4: Predicting in-hospital mortality—ADM is independent from Apache and provides additional prognostic information
Figure 5:
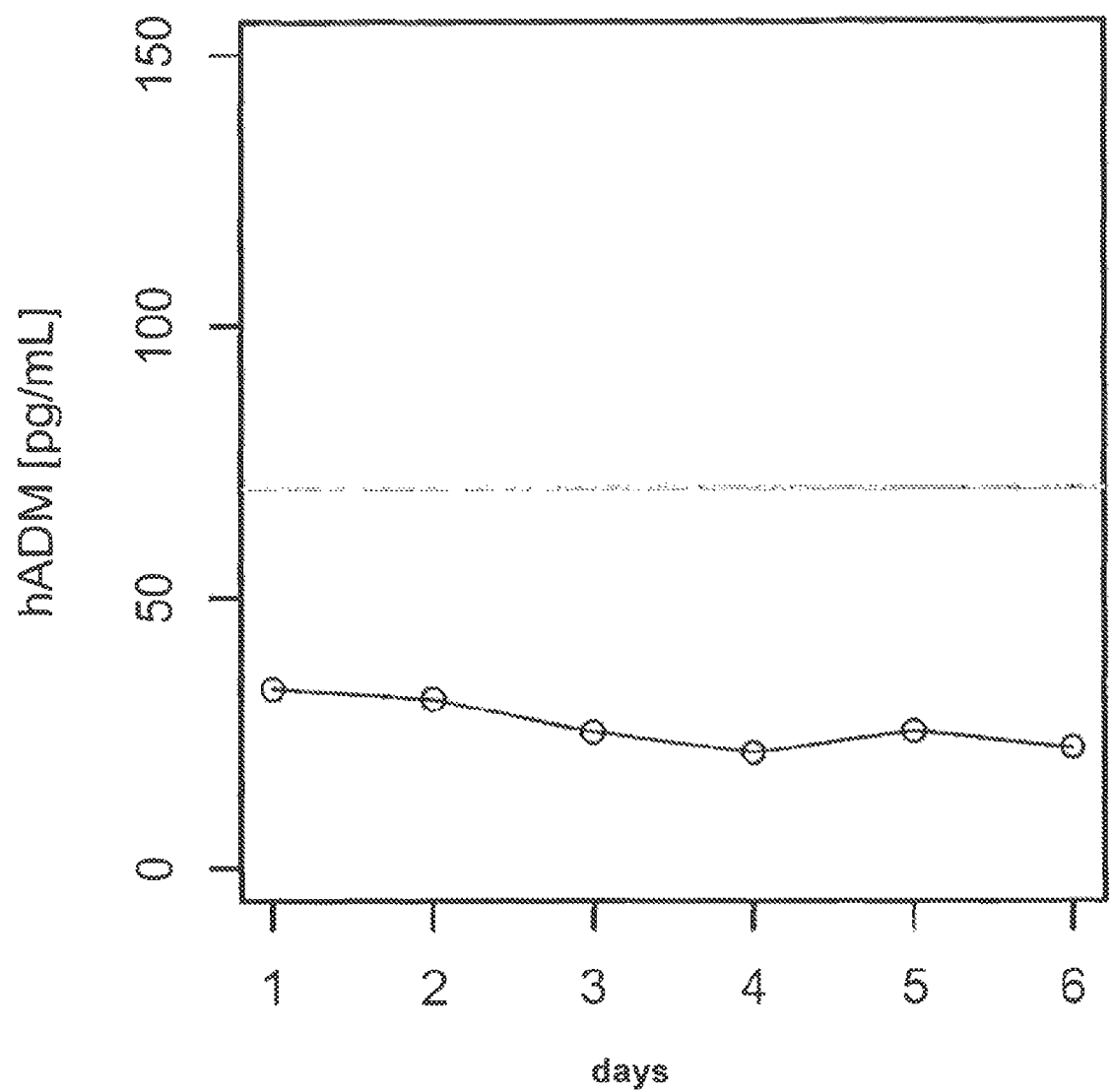
FIGS. 5 to 10: Individual patient ADM-kinetics
Figure 6:
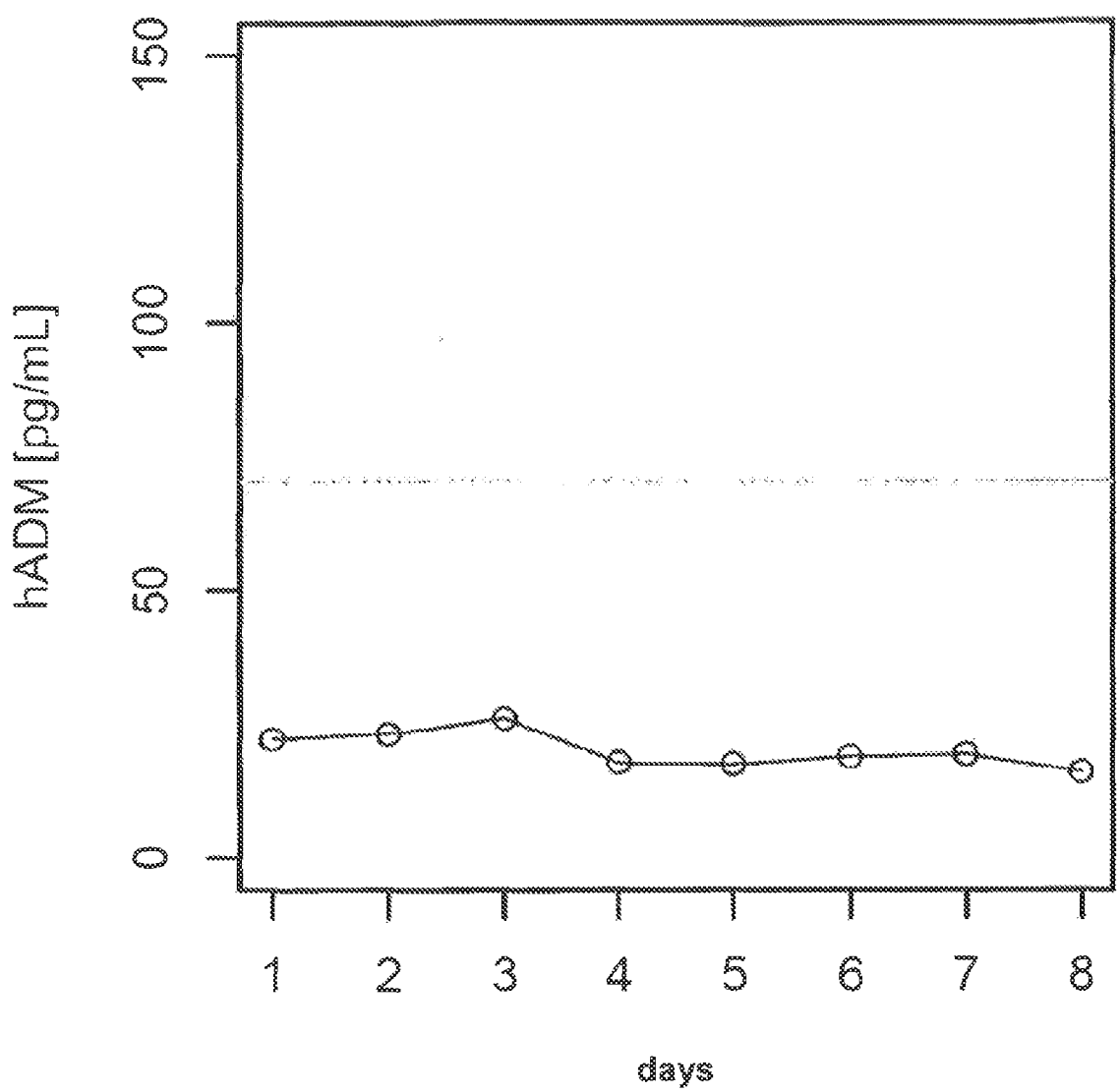
Figure 7:
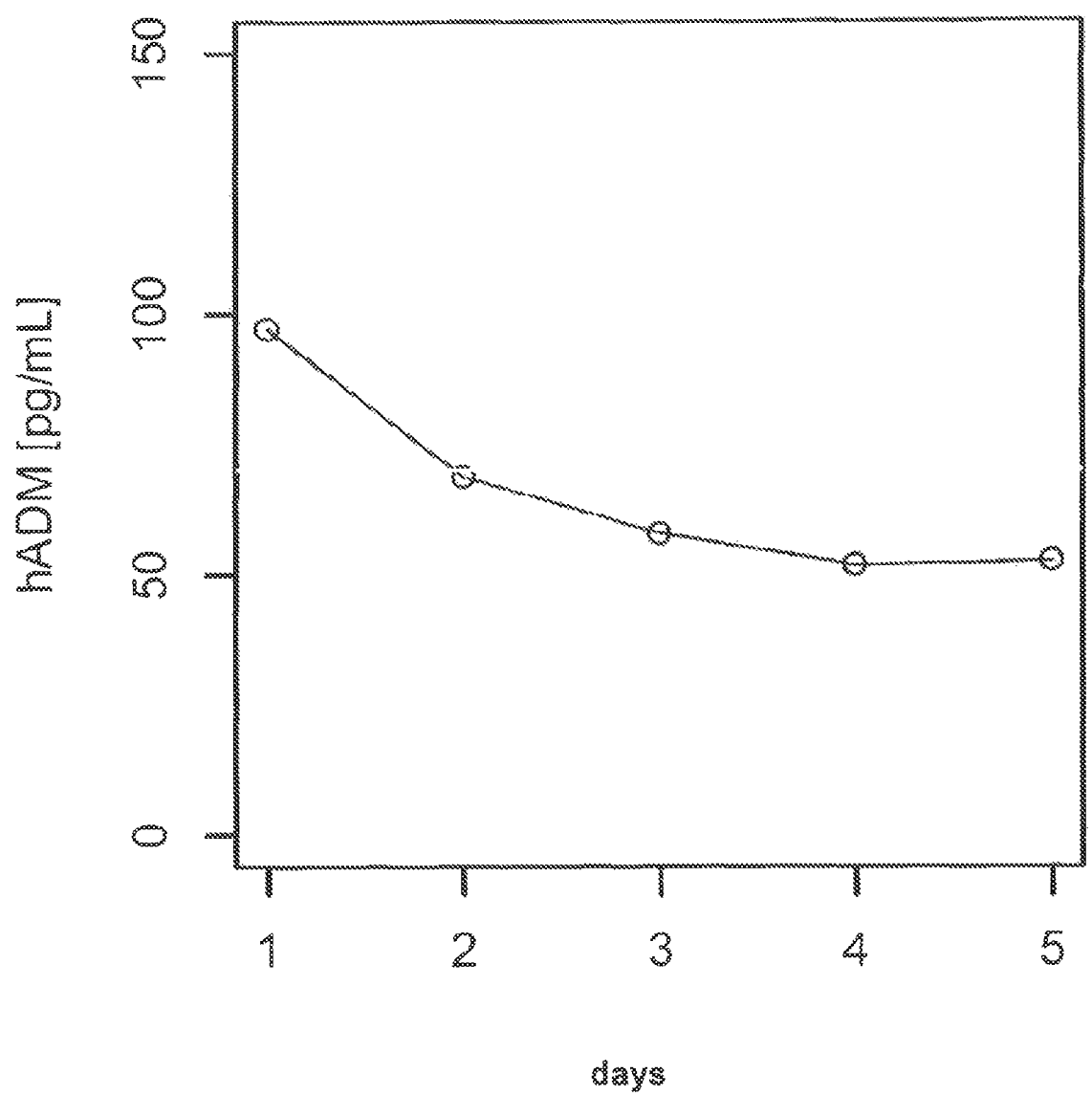
Figure 8:
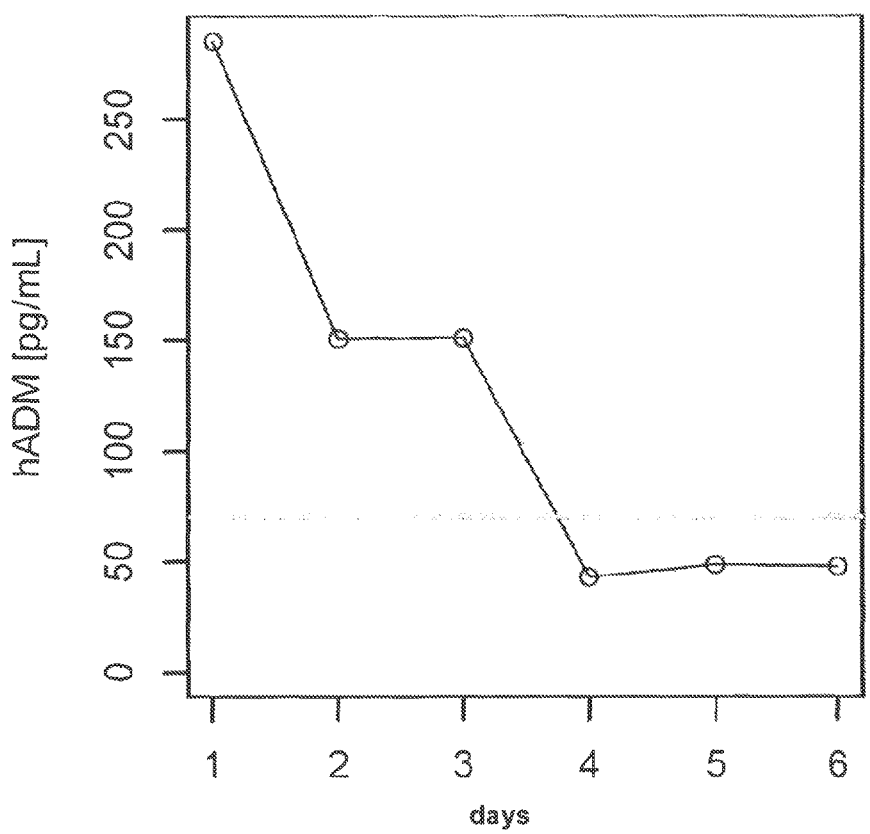
Figure 9:
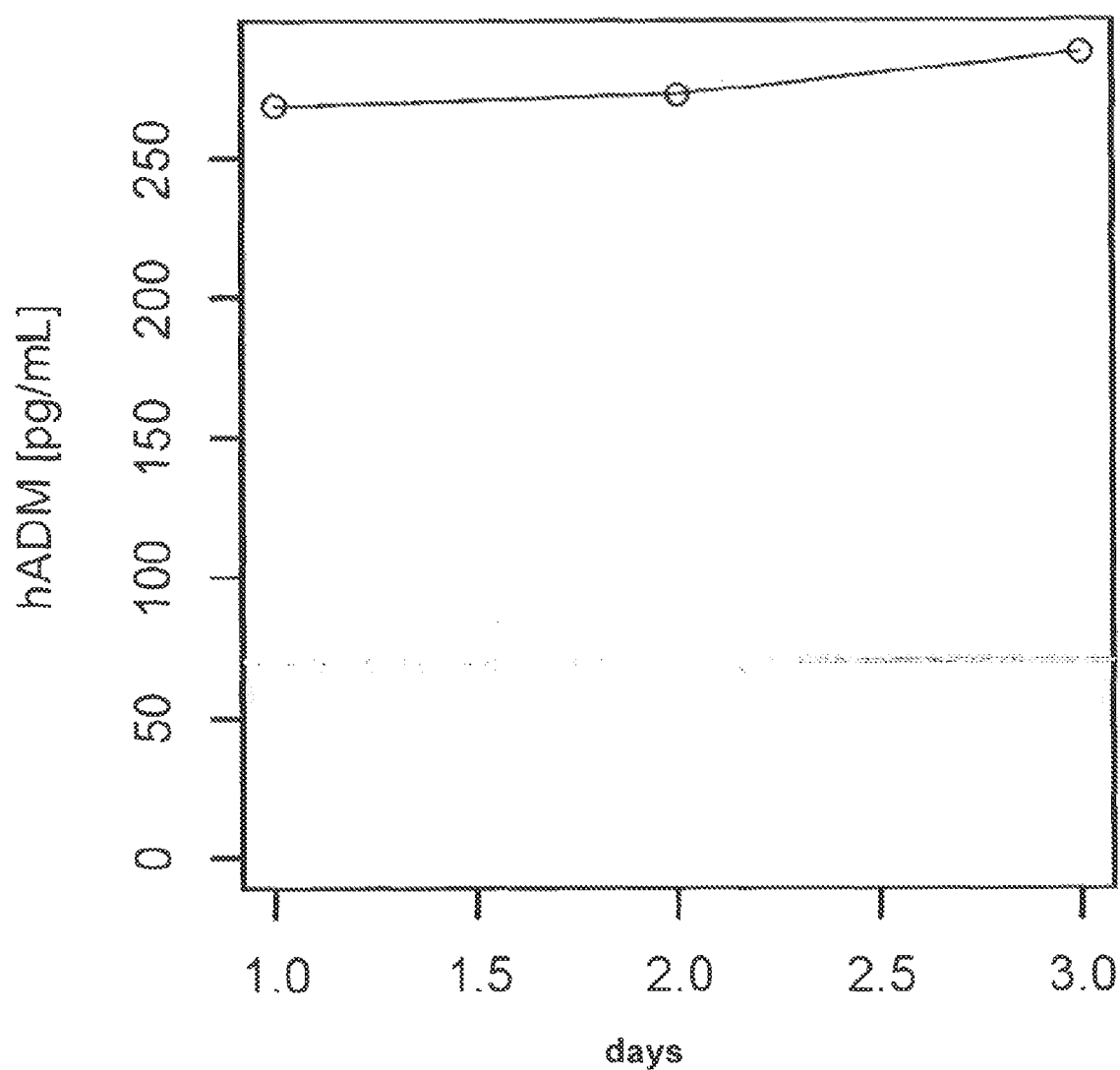
Figure 10:
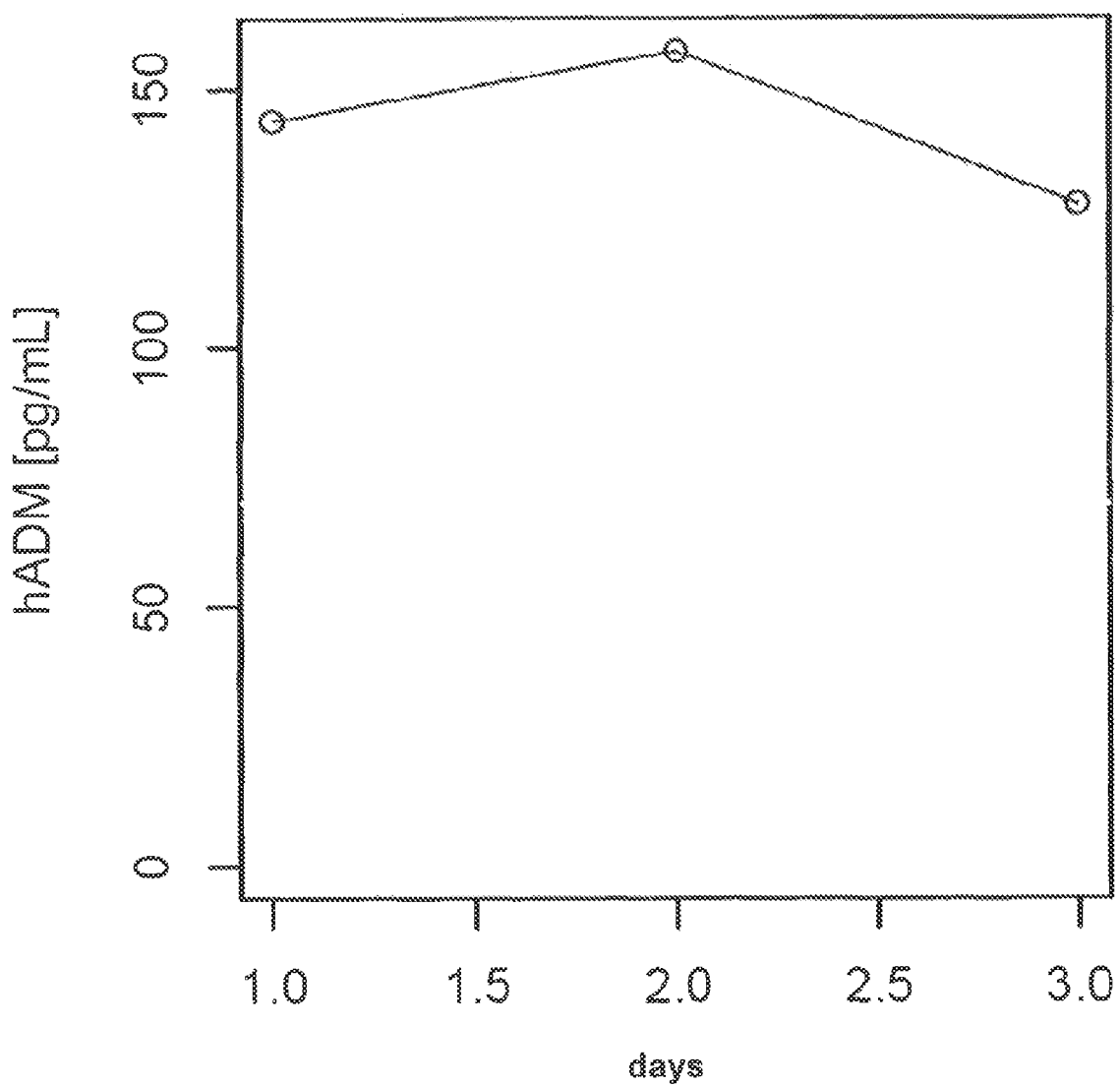
Figure 11:
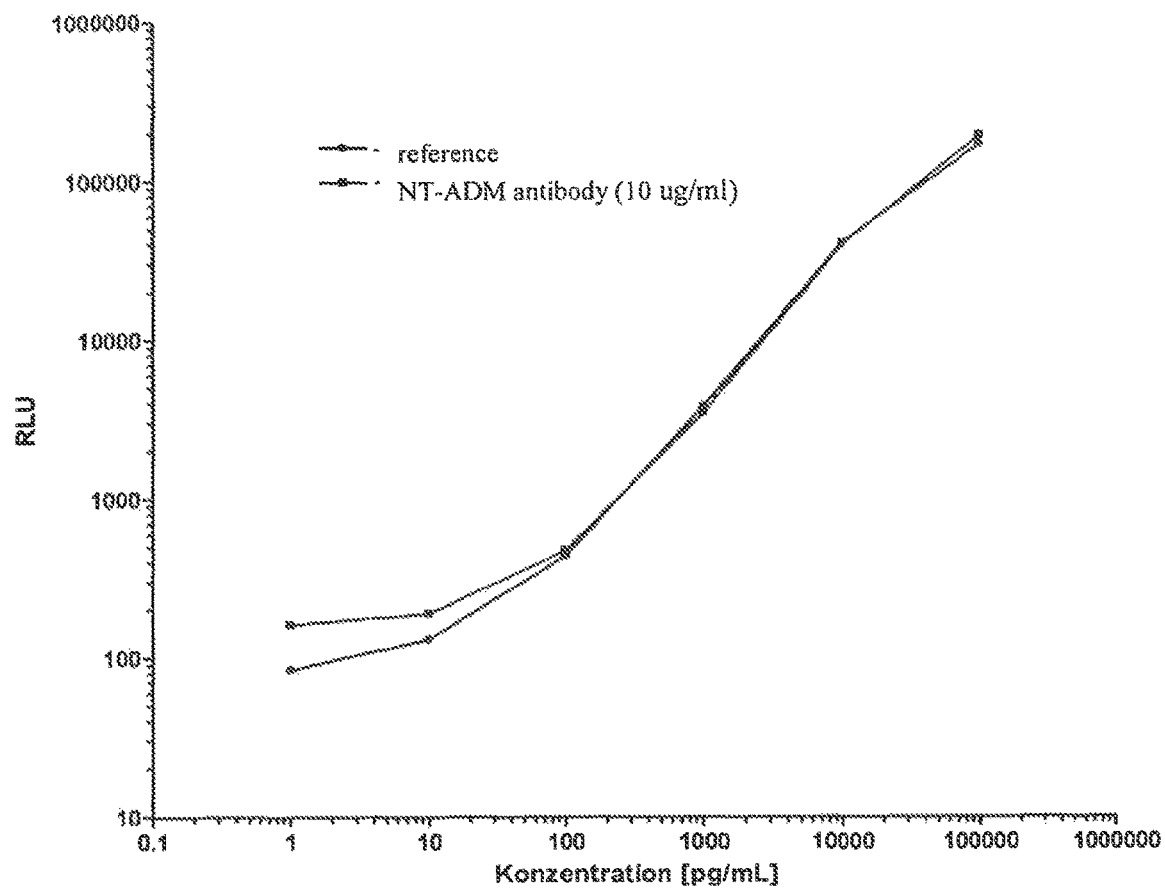
FIG. 11: ADM assay in the presence and absence of N-terminal antibodies

The ADM assay was performed as described above. A) reference curve B) in the presence of NT-ADM-antibody (10 ug/ml, 3.33 ug/test). The addition of NT-ADM-antibody did not influence the ADM assay.

SEQUENCES

SEQ ID No. 1: ADM 21-52
CTVQKLAHQIYQFTDKDKDNVAPRSKISPQGY-CONH2

SEQ ID No. 2: ADM 21-52-Gly
CTVQKLAHQIYQFTDKDKDNVAPRSKISPQGYG

SEQ ID No. 3: PreProADM
MKLVSVALMYLGSLAFLGADTARLDVASEFRKKWNKWALSRGKRELRMSSSYPTGLA
DVKAGPAQTLIRPQDMKGASRSPEDSSPDAARIRVKRYRQSMNNFQGLRSFGCRFGTCT
VQKLAHQIYQFTDKDKDNVAPRSKISPQGYGRRRRRSLPEAGPGRTLVSSKPQAHGAPA
PPSGSAPHFL

SEQ ID No. 4: ADM 1-52
YRQSMNNFQGLRSFGCRFGTCTVQKLAHQIYQFTDKDKDNVAPRSKISPQGY-CONH2

SEQ ID No. 5: ADM 1-52-Gly
YRQSMNNFQGLRSFGCRFGTCTVQKLAHQIYQFTDKDKDNVAPRSKISPQGYG

SEQ ID No. 6: ADM 21-32
CTVQKLAHQIYQ

SEQ ID No. 7: ADM 42-52
APRSKISPQGY

SEQ ID No. 8: ADM 1-16-Gly (amino acid)
YRQSMNNFQGLRSFG

The invention claimed is:

1. An in vitro method for therapy follow-up comprising: forming a complex in a plasma or whole blood sample from a human patient suspected of having sepsis, said complex comprising mature adrenomedullin (ADM) 1-52 and/or mature ADM 1-52-Gly in said sample of plasma or whole blood of said human patient suspected of having sepsis and two antibodies that bind to two different regions within the region of mature adrenomedullin and/or adrenomedullin-Gly that is SEQ ID No. 1 or SEQ ID No. 2 wherein each of said regions comprises at least 4 or 5 amino acids, and
measuring the amount of complex formed and
treating the human patient suspected of having sepsis.

2. The in vitro method for therapy follow-up according to claim 1 wherein one of said antibodies binds to a region within SEQ ID No. 4 and wherein said second of these antibodies binds to a region within SEQ ID No. 5.

3. The in vitro method for therapy follow-up according to claim 1 wherein the measurement is determined in an assay which is able to quantify the ADM of healthy subjects and is <10 pg/ml.

4. The in vitro method for therapy follow-up according to claim 1 wherein one of said antibodies exhibits an binding affinity to mature ADM and/or mature ADM 1-52-Gly of at least $10^7$ M$^{-1}$.

5. The in vitro method for therapy follow-up according to claim 1 wherein one of said antibodies is an anti-adrenomedullin antibody or an anti-ADM antibody fragment binding to ADM or a non-Ig scaffold binding to adrenomedullin.

6. The in vitro method for therapy follow-up according to claim 1 wherein said measurement is determined in a sandwich assay.

7. The in vitro method for therapy follow-up according to claim 1 wherein at least one of said two antibodies is labeled in order to be detected.

8. The in vitro method for therapy follow-up according to claim 1 wherein at least one of said two antibodies is bound to a solid phase.

9. The in vitro method for therapy follow-up according to claim 7 wherein said label is a chemiluminescent label, an enzyme label, a fluorescence label or a radioiodine label.

10. The in vitro method for therapy follow-up according to claim 1 wherein the concentration of mature ADM 1-52 and/or mature ADM 1-52-Gly complex measured in the sample is in the range between 10-500 pg/ml.

11. The in vitro method for therapy follow-up according to claim 1 wherein said sample is selected from the group comprising human citrate plasma, heparin plasma, EDTA plasma, whole blood.

12. The in vitro method for therapy follow-up according to claim 11 wherein said complex is directly measured without any further sample preparation.

13. The in vitro method for therapy follow-up according to claim 1 wherein said method is performed on a fully automated device.

14. The in vitro method for therapy follow-up according to claim 1 wherein mature ADM 1-52 and/or mature ADM 1-52-Gly is detecting in at least two samples wherein said samples are taken in different points of time from said septic human patients.

15. The in vitro method for therapy follow-up according to claim 1 wherein the sample volume measured is less or equal to 50 ul.

16. The in vitro method for therapy follow-up according to claim 3, wherein the assay sensitivity of said assay is able to quantify the ADM of healthy subjects and is <40 pg/ml.

17. The in vitro method for therapy follow-up according to claim 3, wherein the assay sensitivity of said assay is able to quantify the ADM of healthy subjects and is <70 pg/ml.

18. The method of claim 1, wherein a threshold value below 70 pg/ml is indicative of a human patient responding to therapy.

* * * * *

SEQUENCE LISTING

<160> NUMBER OF SEQ ID NOS: 8

<210> SEQ ID NO 1
<211> LENGTH: 32
<212> TYPE: PRT
<213> ORGANISM: Homo sapiens

<400> SEQUENCE: 1

Cys Thr Val Gln Lys Leu Ala His Gln Ile Tyr Gln Phe Thr Asp Lys
1               5                   10                  15

Asp Lys Asp Asn Val Ala Pro Arg Ser Lys Ile Ser Pro Gln Gly Tyr
            20                  25                  30

<210> SEQ ID NO 2
<211> LENGTH: 33
<212> TYPE: PRT
<213> ORGANISM: Homo sapiens

<400> SEQUENCE: 2

Cys Thr Val Gln Lys Leu Ala His Gln Ile Tyr Gln Phe Thr Asp Lys
1               5                   10                  15

Asp Lys Asp Asn Val Ala Pro Arg Ser Lys Ile Ser Pro Gln Gly Tyr
            20                  25                  30

Gly

<210> SEQ ID NO 3
<211> LENGTH: 185
<212> TYPE: PRT
<213> ORGANISM: Homo sapiens

<400> SEQUENCE: 3

Met Lys Leu Val Ser Val Ala Leu Met Tyr Leu Gly Ser Leu Ala Phe
1               5                   10                  15

Leu Gly Ala Asp Thr Ala Arg Leu Asp Val Ala Ser Glu Phe Arg Lys
            20                  25                  30

```
Lys Trp Asn Lys Trp Ala Leu Ser Arg Gly Lys Arg Glu Leu Arg Met
         35                  40                  45

Ser Ser Ser Tyr Pro Thr Gly Leu Ala Asp Val Lys Ala Gly Pro Ala
 50                  55                  60

Gln Thr Leu Ile Arg Pro Gln Asp Met Lys Gly Ala Ser Arg Ser Pro
 65                  70                  75                  80

Glu Asp Ser Ser Pro Asp Ala Ala Arg Ile Arg Val Lys Arg Tyr Arg
                 85                  90                  95

Gln Ser Met Asn Asn Phe Gln Gly Leu Arg Ser Phe Gly Cys Arg Phe
                100                 105                 110

Gly Thr Cys Thr Val Gln Lys Leu Ala His Gln Ile Tyr Gln Phe Thr
            115                 120                 125

Asp Lys Asp Lys Asp Asn Val Ala Pro Arg Ser Lys Ile Ser Pro Gln
130                 135                 140

Gly Tyr Gly Arg Arg Arg Arg Ser Leu Pro Glu Ala Gly Pro Gly
145                 150                 155                 160

Arg Thr Leu Val Ser Ser Lys Pro Gln Ala His Gly Ala Pro Ala Pro
                165                 170                 175

Pro Ser Gly Ser Ala Pro His Phe Leu
                180                 185

<210> SEQ ID NO 4
<211> LENGTH: 52
<212> TYPE: PRT
<213> ORGANISM: Homo sapiens

<400> SEQUENCE: 4

Tyr Arg Gln Ser Met Asn Asn Phe Gln Gly Leu Arg Ser Phe Gly Cys
  1               5                  10                  15

Arg Phe Gly Thr Cys Thr Val Gln Lys Leu Ala His Gln Ile Tyr Gln
                 20                  25                  30

Phe Thr Asp Lys Asp Lys Asp Asn Val Ala Pro Arg Ser Lys Ile Ser
             35                  40                  45

Pro Gln Gly Tyr
 50

<210> SEQ ID NO 5
<211> LENGTH: 53
<212> TYPE: PRT
<213> ORGANISM: Homo sapiens

<400> SEQUENCE: 5

Tyr Arg Gln Ser Met Asn Asn Phe Gln Gly Leu Arg Ser Phe Gly Cys
  1               5                  10                  15

Arg Phe Gly Thr Cys Thr Val Gln Lys Leu Ala His Gln Ile Tyr Gln
                 20                  25                  30

Phe Thr Asp Lys Asp Lys Asp Asn Val Ala Pro Arg Ser Lys Ile Ser
             35                  40                  45

Pro Gln Gly Tyr Gly
 50

<210> SEQ ID NO 6
<211> LENGTH: 12
<212> TYPE: PRT
<213> ORGANISM: Homo sapiens

<400> SEQUENCE: 6

Cys Thr Val Gln Lys Leu Ala His Gln Ile Tyr Gln
```

```
1               5               10

<210> SEQ ID NO 7
<211> LENGTH: 11
<212> TYPE: PRT
<213> ORGANISM: Homo sapiens

<400> SEQUENCE: 7

Ala Pro Arg Ser Lys Ile Ser Pro Gln Gly Tyr
1               5                   10

<210> SEQ ID NO 8
<211> LENGTH: 16
<212> TYPE: PRT
<213> ORGANISM: Homo sapiens

<400> SEQUENCE: 8

Tyr Arg Gln Ser Met Asn Asn Phe Gln Gly Leu Arg Ser Phe Gly Cys
1               5                   10                  15
```